(12) United States Patent
Bobey et al.

(10) Patent No.: US 8,117,701 B2
(45) Date of Patent: Feb. 21, 2012

(54) CONTROL UNIT FOR PATIENT SUPPORT

(75) Inventors: John A. Bobey, Daniel Island, SC (US);
Stephen L. Douglas, Batesville, IN (US); Eric R. Meyer, Greensburg, IN (US); Jonathan H. Mueller, Mt. Pleasant, SC (US); Robert Petrosenko, Calgary (CA); Stephen R. Schulte, Gibsonia, PA (US); Andrew F. Skinner, Batesville, IN (US); Michael Z. Sleva, Atlanta, GA (US); Richard B. Stacy, Daniel Island, SC (US); Daniel K. Stevens, Summerville, SC (US); Mayur Yermaneni, Shrewsbury, MA (US)

(73) Assignee: Hill-Rom Services, Inc., Batesville, IN (US)

( * ) Notice: Subject to any disclaimer, the term of this patent is extended or adjusted under 35 U.S.C. 154(b) by 697 days.

(21) Appl. No.: 11/994,478

(22) PCT Filed: Jul. 7, 2006

(86) PCT No.: PCT/US2006/026788
§ 371 (c)(1),
(2), (4) Date: Oct. 8, 2008

(87) PCT Pub. No.: WO2007/008831
PCT Pub. Date: Jan. 18, 2007

(65) Prior Publication Data
US 2009/0237264 A1  Sep. 24, 2009

Related U.S. Application Data

(60) Provisional application No. 60/697,708, filed on Jul. 8, 2005.

(51) Int. Cl.
*A47C 27/08* (2006.01)

(52) U.S. Cl. ............... 5/713; 5/600; 5/905; 340/825.69
(58) Field of Classification Search ............ 5/713, 600, 5/905, 425, 616, 658, 710, 706, 625; 340/815.69
See application file for complete search history.

(56) References Cited

U.S. PATENT DOCUMENTS 5,713,856 A  2/1998  Eggers et al.
(Continued)

FOREIGN PATENT DOCUMENTS

JP  02-141441 U  11/1990
(Continued)

OTHER PUBLICATIONS

Australian official action from related AU 2006268288, dated Oct. 18, 2011, 2 pages.
(Continued)

*Primary Examiner* — Robert G Santos
*Assistant Examiner* — Brittany Wilson
(74) *Attorney, Agent, or Firm* — Barnes & Thornburg LLP

(57) ABSTRACT

This disclosure describes a control unit for a patient support, such as a mattress. One embodiment of the control unit includes a base portion and a display portion pivotably coupled to the base portion. The control unit may also include one or more communication ports for sending or receiving data from one or more remote devices over a network. The control unit may also include a memory port into which memory may be removably inserted. The control unit may also include a visual indicator configured to be activated by a triggering event, such as a patient exiting the mattress. The display unit may include a touchscreen user interface. The display unit may also be configured to display audiovisual material.

24 Claims, 34 Drawing Sheets

U.S. PATENT DOCUMENTS

| | | |
|---|---|---|
| 6,771,181 B1 | 8/2004 | Hughen, Jr. |
| 6,829,796 B2 | 12/2004 | Salvatini et al. |
| 7,861,334 B2 * | 1/2011 | Lemire et al. ............... 5/53.1 |
| 2003/0061664 A1 * | 4/2003 | Salvatini et al. ............ 5/713 |
| 2003/0197614 A1 | 10/2003 | Smith et al. |
| 2007/0157385 A1 * | 7/2007 | Lemire et al. ............... 5/600 |
| 2007/0163043 A1 * | 7/2007 | Lemire et al. ............... 5/600 |
| 2007/0169268 A1 * | 7/2007 | Lemire et al. ............... 5/617 |
| 2007/0174965 A1 * | 8/2007 | Lemire et al. ............... 5/600 |
| 2007/0268480 A1 * | 11/2007 | Kaye ........................ 356/138 |

FOREIGN PATENT DOCUMENTS

| | | |
|---|---|---|
| JP | 03-047860 B2 | 2/1991 |
| JP | 2003-164496 A | 6/2003 |
| JP | 2003-524483 A | 8/2003 |
| JP | 2004-141484 A | 5/2004 |
| JP | 2005-118147 A | 5/2005 |
| WO | 01/47340 A2 | 7/2001 |

OTHER PUBLICATIONS

Official action for AU 2006268288 dated Dec. 8, 2010, 3 pages.

Official action (in Japanese and English language translation) for JP 2008-520446 dated Jul. 26, 2011, 8 pages.

PCT International Search Report for PCT/US2006/026788 completed by the US Searching Authority on Apr. 3, 2007.

* cited by examiner

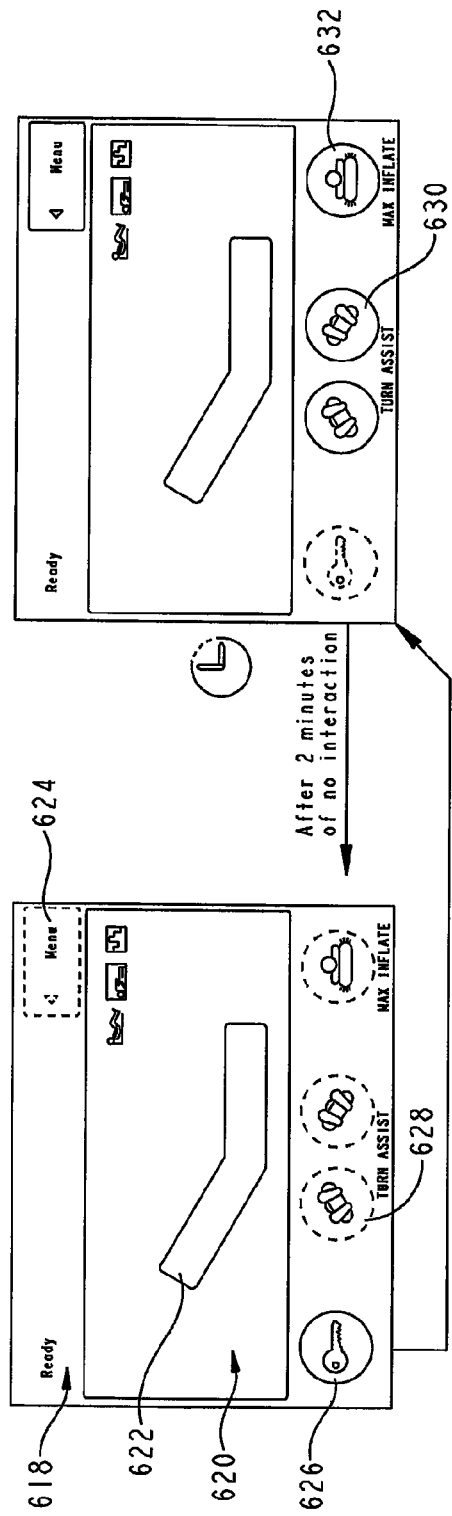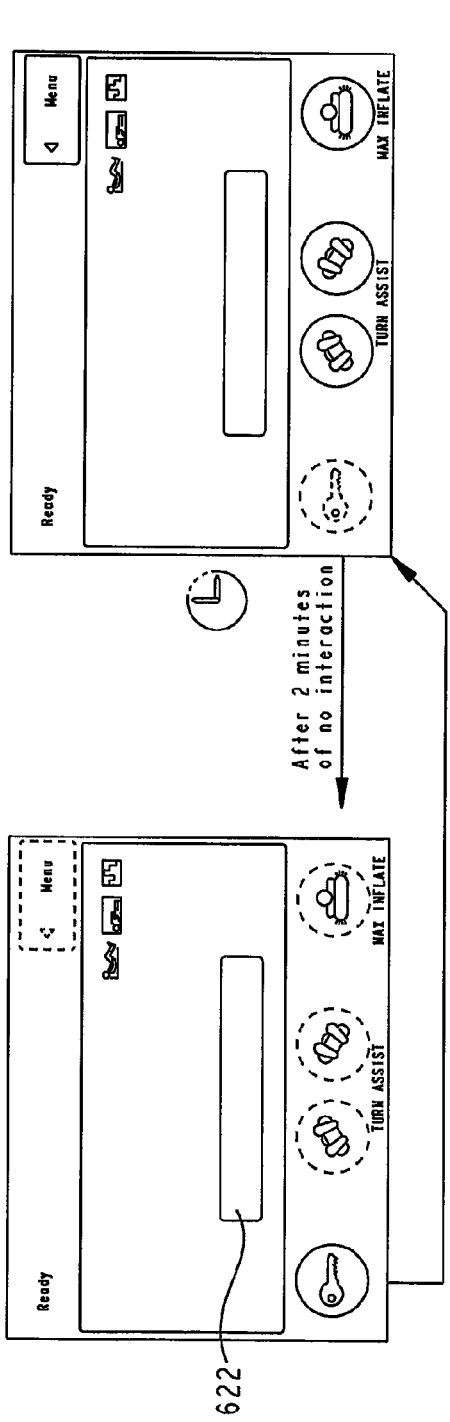
FIG. 22A  FIG. 22B  FIG. 22C  FIG. 22D

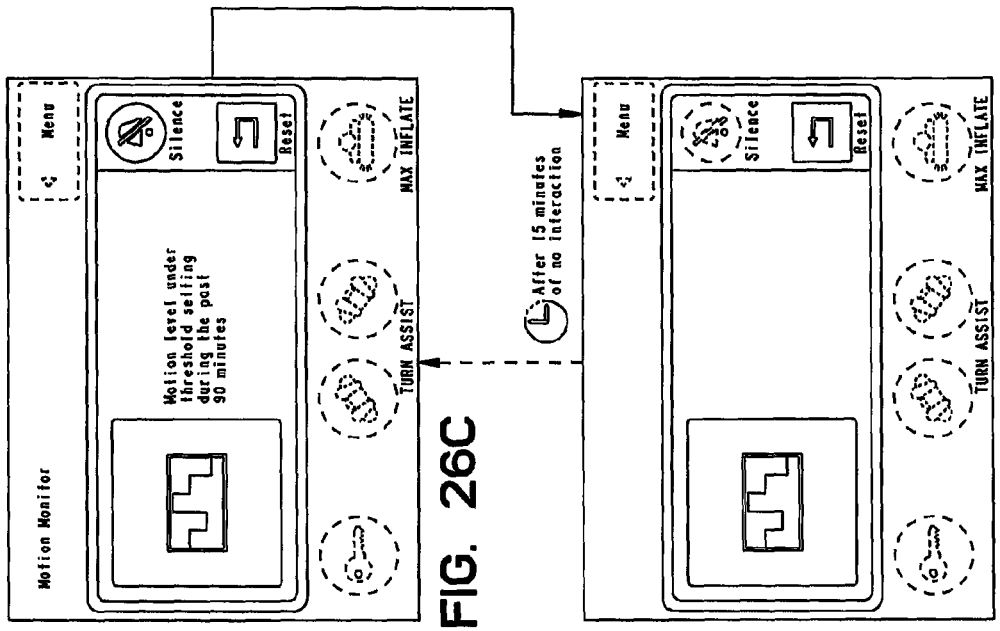
FIG. 26C
FIG. 26D
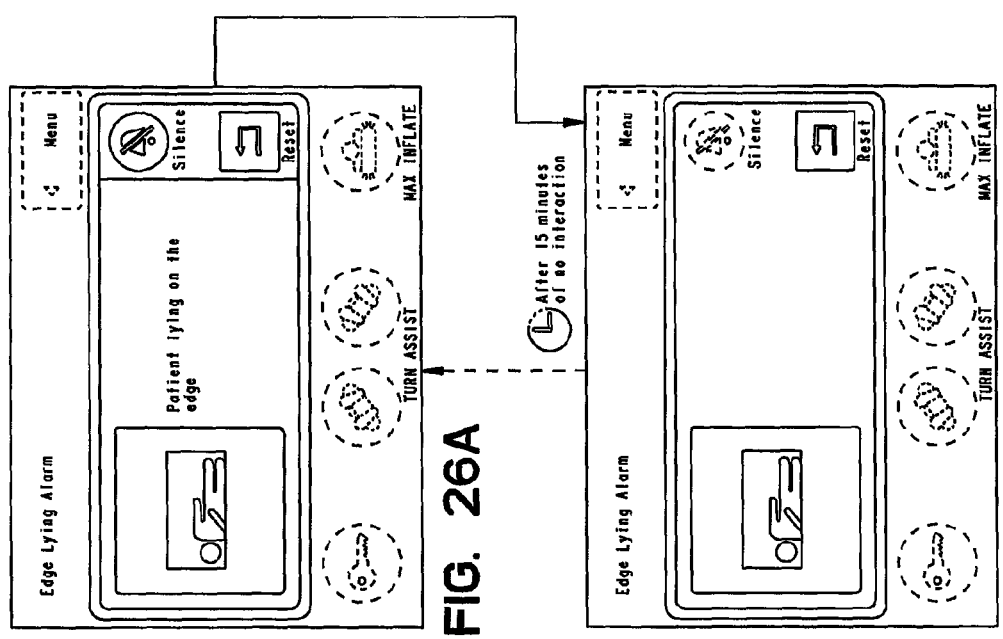
FIG. 26A
FIG. 26B

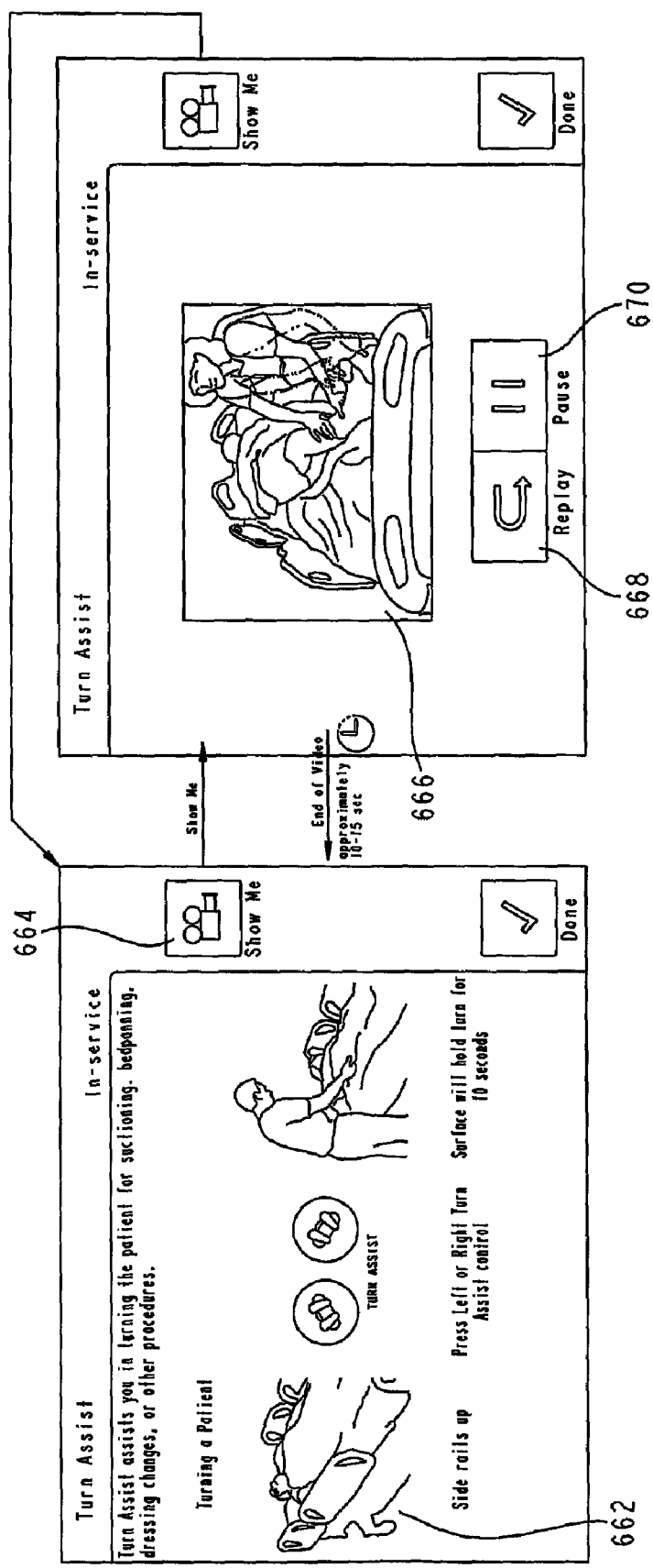

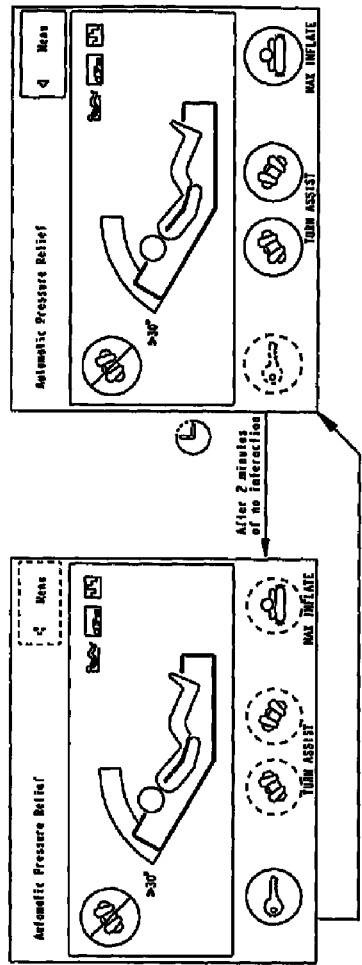
FIG. 30A
FIG. 30B
FIG. 30C
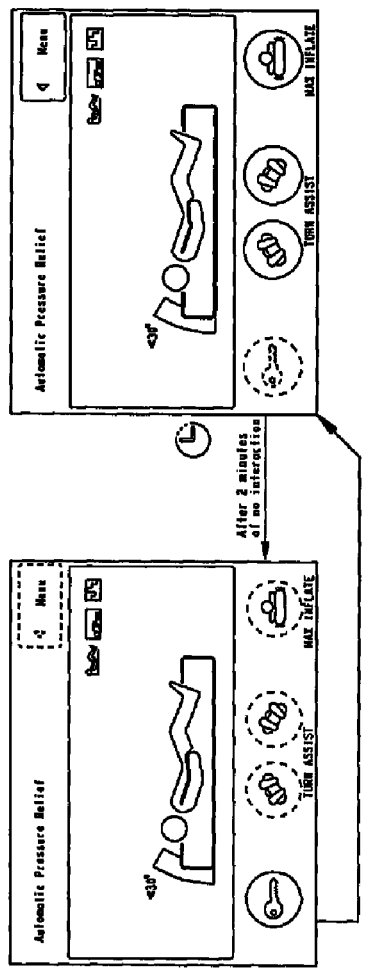
FIG. 30D
FIG. 30E
FIG. 30F

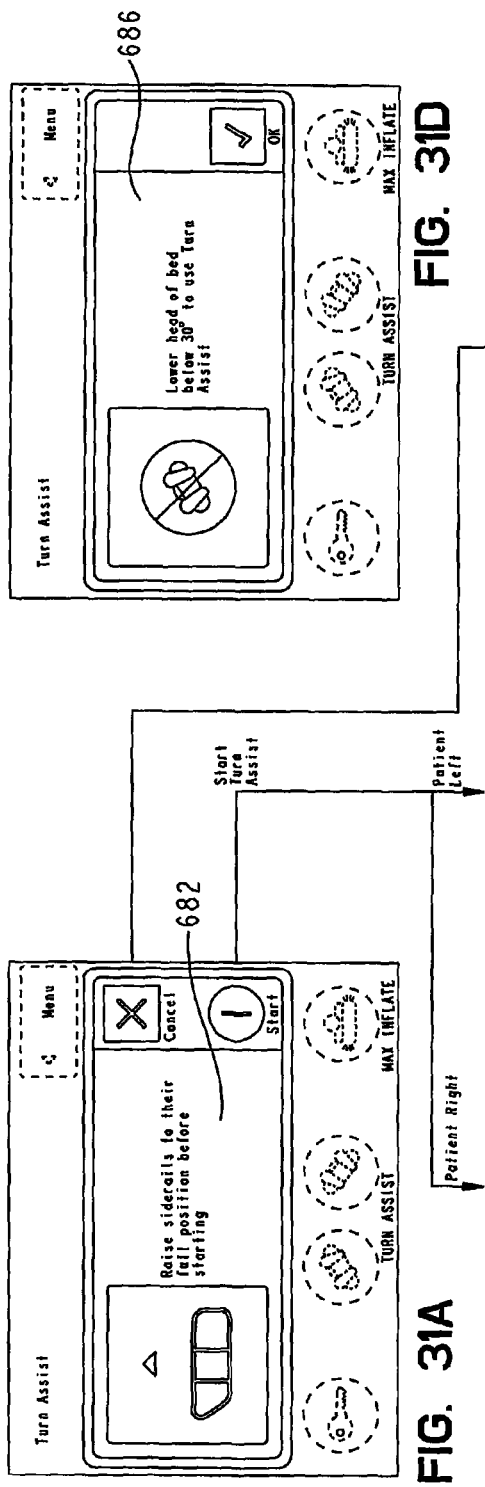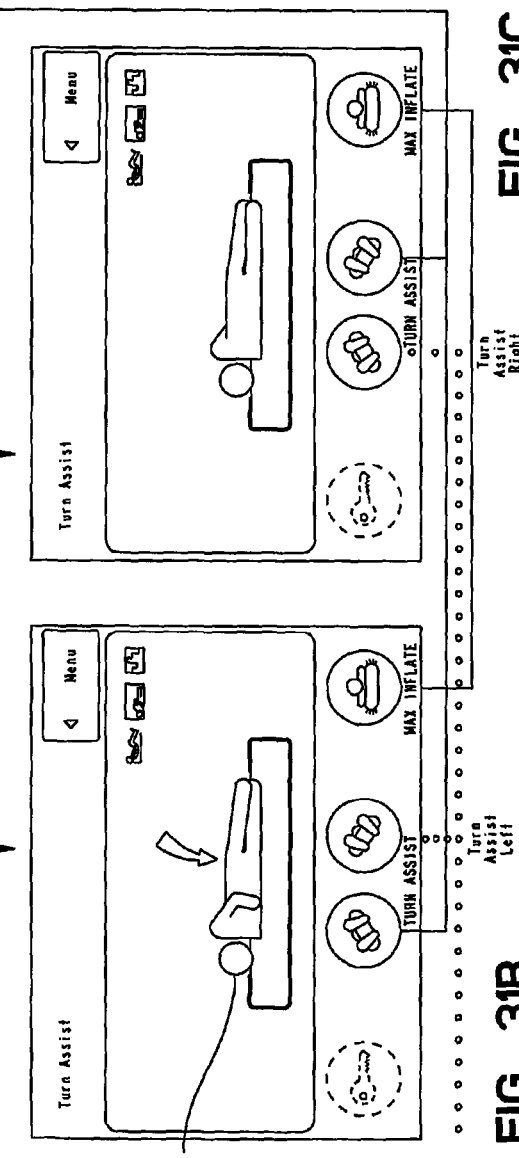
FIG. 31A  FIG. 31B  FIG. 31C  FIG. 31D

CONTROL UNIT FOR PATIENT SUPPORT

CROSS-REFERENCE TO RELATED APPLICATIONS

This application is the U.S. national phase of PCT/US2006/026788 filed Jul. 7, 2006. PCT/US2006/026788 claims priority to U.S. Provisional Patent Application No. 60/697,708 filed Jul. 8, 2005. The entire disclosures of both of PCT/US2006/026788 and U.S. Ser. No. 60/697,708 are hereby incorporated by reference. The present application is related to U.S. patent application Ser. No. 11/119,980, entitled PRESSURE RELIEF SURFACE, and U.S. patent application Ser. No. 11/119,991, entitled PATIENT SUPPORT HAVING REAL TIME PRESSURE CONTROL, and U.S. patent application Ser. No. 11/119,635, entitled LACK OF PATIENT MOVEMENT MONITOR AND METHOD, and U.S. patent application Ser. No. 11/120,080, entitled PATIENT SUPPORT, all of which were filed on May 2, 2005, all of which are assigned to the assignee of the present invention, and all of which are incorporated herein by this reference.

The present application is also related to U.S. Provisional Patent Application Ser. No. 60/636,252, entitled QUICK CONNECTOR FOR MULTIMEDIA, filed Dec. 15, 2004, which is assigned to the assignee of the present invention and incorporated herein by this reference.

The present application is also related to U.S. Provisional Patent Application Ser. No. 60/697,748, entitled PRESSURE CONTROL FOR A HOSPITAL BED filed Jul. 8, 2005 and corresponding PCT Patent Application Serial No. PCT/US2006/026787, filed the same date herewith, and U.S. Provisional Patent Application Ser. No. 60/697,723, entitled PRESSURE RELIEF SUPPORT SURFACE filed Jul. 8, 2005 and corresponding PCT Patent Application Serial No. PCT/US2006/026620, filed the same date herewith, all of which are incorporated herein by this reference.

The present application is also related to U.S. Provisional Patent Application Ser. No. 60/734,942, entitled PNEUMATIC VALVE ASSEMBLY FOR A PATIENT SUPPORT, filed Nov. 9, 2005, assigned to the assignee of the present invention and incorporated herein by this reference.

BACKGROUND

The present disclosure relates to a control unit for a device for supporting a patient, such as a mattress. In particular, the present disclosure relates to a control unit for a patient support appropriate for use in hospitals, acute care facilities, and other patient care environments.

SUMMARY

A control unit for a patient support is provided. The control unit includes a housing adaptable to be removably coupled to a patient support, the housing defining an interior region including a controller, and an air supply including a first portion operably coupled to the controller to provide high volume, low pressure air to a first interior portion of the patient support, and a second portion operably coupled to the controller to provide low volume, high pressure air to a second interior portion of the patient support.

The first air supply portion may include a blower and the second air supply portion may include a compressor. A hose connector coupled to the air supply may also be included. The hose connector may include a first connector portion coupled to the first air supply portion and a second connector portion coupled to the second air supply portion.

A display portion pivotably coupled to the housing may also be included.

A plurality of communications ports including a wireless connectivity port may also be included.

A memory port configured to receive a removable memory card may also be included.

An identification tag coupled to the housing may also be included.

In another embodiment, a control unit for a patient support is provided. The control unit includes a housing adaptable to be removably coupled to a patient support, the housing defining an interior region including a controller and an air supply, and a display portion pivotably coupled to the housing, the display portion being movable with respect to the housing between a raised position and a lowered position, the display portion including a video display and a touchscreen user interface.

The display portion may include a wireless access port. The display portion may include a memory port configured to receive removable memory.

A friction hinge coupled between the display portion and the housing may also be included.

The angle of the display portion with respect to the housing when the display portion is in the raised position may be at least 180 degrees.

A detent configured to hold the display portion in the lowered position may also be included.

The user interface may include a graphical depiction of a patient support which varies based on the presence or absence of a patient on the patient support.

In yet another embodiment, a control unit for a patient support is provided. The control unit includes a housing adaptable to be coupled to a patient support, the housing defining an interior region, a controller located in the interior region, a user interface coupled to the housing, and a light bar coupled to the housing, the light bar being controllable by the controller to selectively illuminate in one of a plurality of modes.

Each of the plurality of modes may be indicative of a different operating condition of the control unit. The light bar may illuminate in a first mode if the patient support is in CPR position. The light bar may illuminate in a second mode if the control unit is in need of service. The light bar may illuminate in a third mode if the control unit is powered on and operating normally. The light bar may illuminate in a fourth mode if an alarm is activated. The light bar may be illuminated in a different color and/or intermittently (i.e. flashing) to indicate a particular operational mode, or for other reasons.

In still another embodiment, a control unit for a patient support is provided. The control unit includes a base portion including a controller and an air supply, and a display portion configured to display a graphical user interface including at least one graphical depiction that automatically changes in response to a change in an operating condition of the patient support.

The graphical depiction may be of a patient support and the graphical depiction may change automatically in response to a person being positioned on the patient support. The graphical depiction may be of a patient support and the graphical depiction may change automatically in response to articulation of a portion of the patient support. The graphical depiction may be of a patient support and the graphical depiction may change automatically in response to a change in inflation of the patient support. The graphical depiction may be of a pressure map for a patient support and the pressure map may change automatically in response to patient movement.

BRIEF DESCRIPTION OF THE DRAWINGS

Aspects of the present invention are more particularly described below with reference to the following figures, which illustrate exemplary embodiments of the present invention:

FIGS. 22 A-D are exemplary user interfaces for a main display screen of a control unit;

FIGS. 26 A-D are exemplary user interfaces for configuring other alarm types;

FIGS. 29 A-B are exemplary user interfaces for viewing instructional material relating to a patient support;

FIGS. 30 A-F are exemplary user interfaces for monitoring a pressure relief feature;

FIGS. 31 A-D are exemplary user interfaces for monitoring a turn-assist feature;

Figure 1:
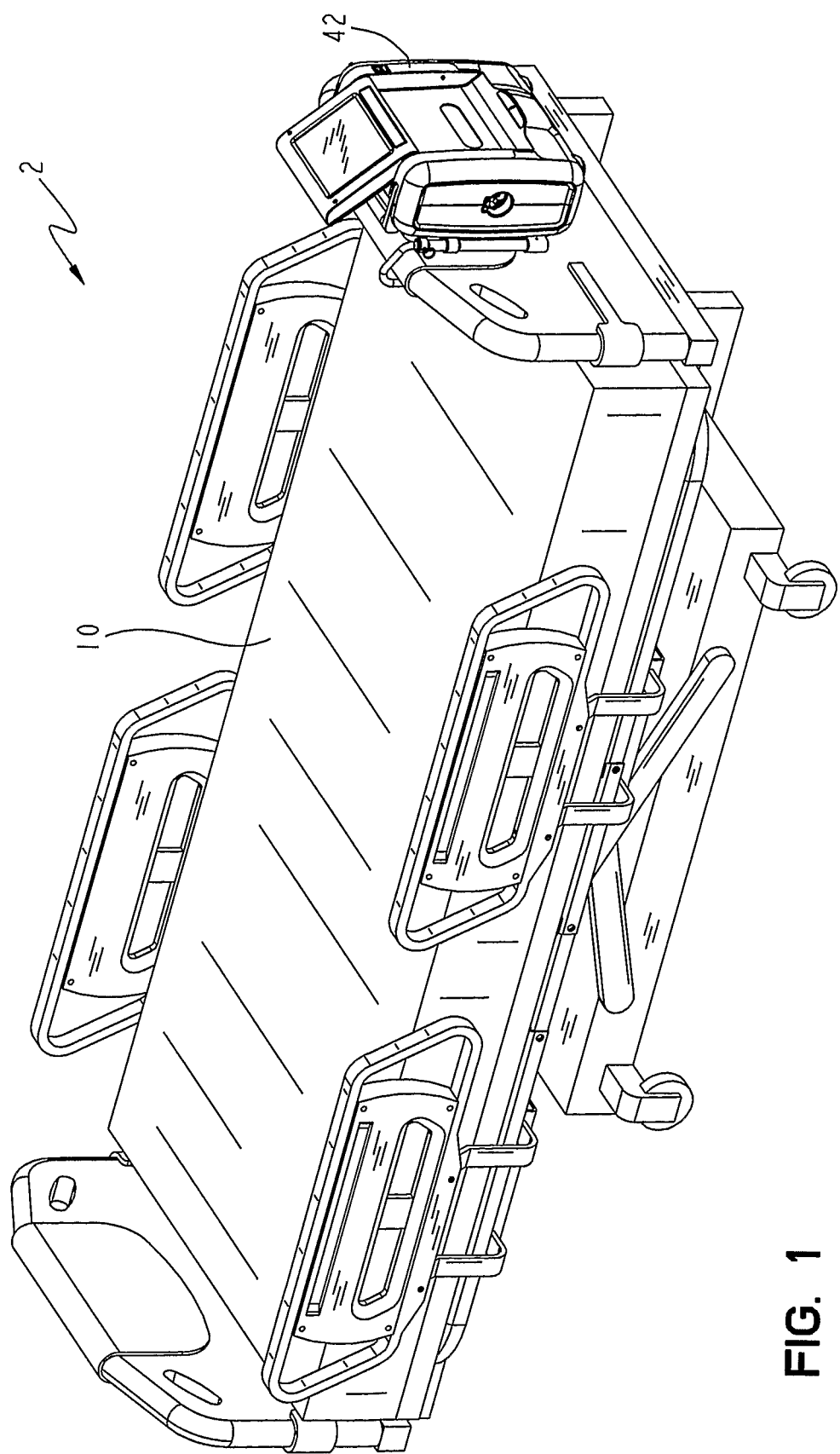
FIG. 1 is a perspective view of a control unit in accordance with the present invention, shown supported by a footboard portion of an exemplary hospital bed.

Corresponding reference characters indicate corresponding parts throughout the several views. Although the exemplification set out herein illustrates an embodiment of the invention, in one form, the embodiment disclosed below is not intended to be exhaustive or to be construed as limiting the scope of the invention to the precise form disclosed.

DETAILED DESCRIPTION

FIG. 1 shows an embodiment of a control unit 42 positioned on an exemplary bed 2. Control unit 42 is configured to control certain automated features of mattress 10. Mattress 10 may be any suitable mattress having one or more automated features.

Figure 2:
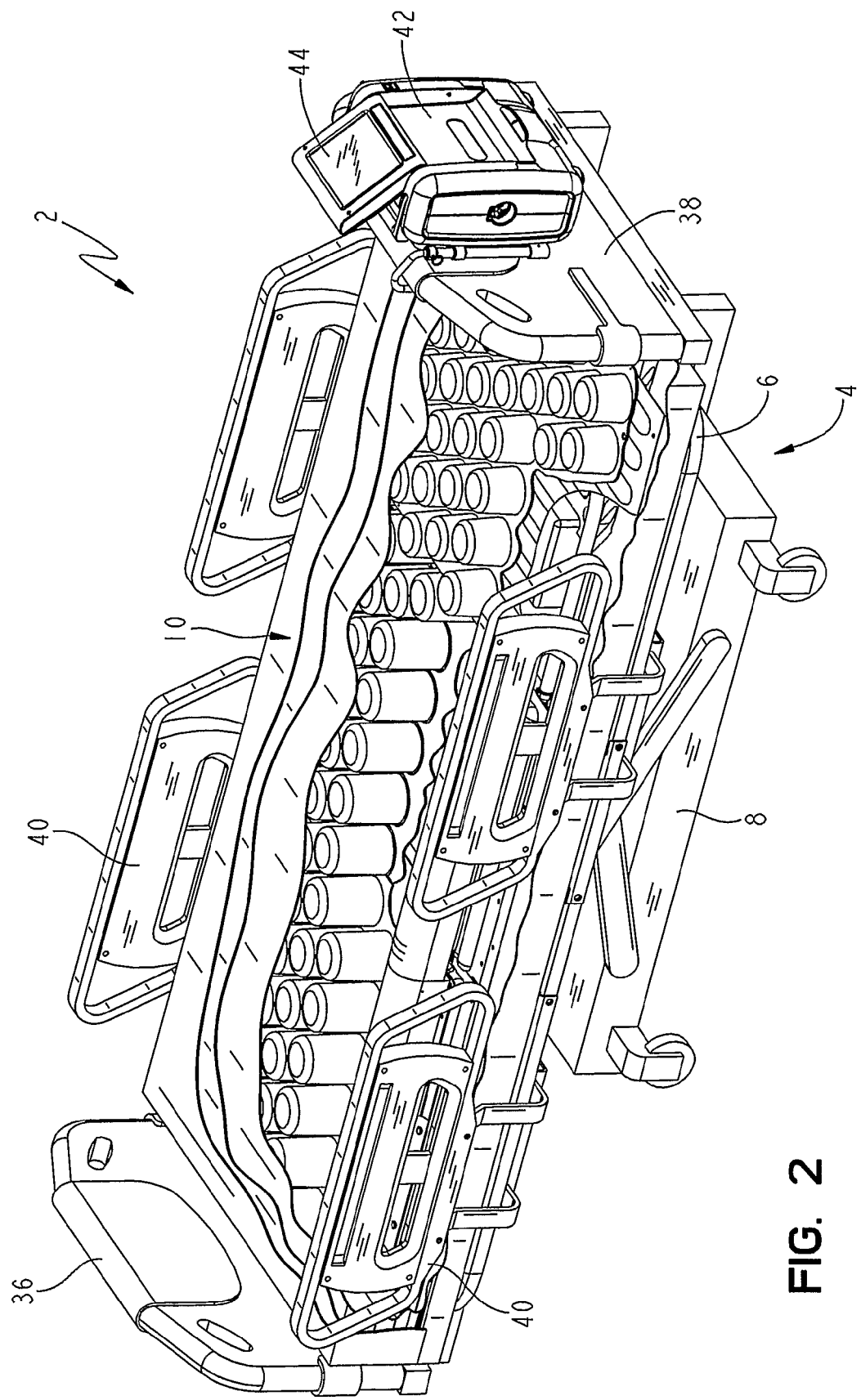
FIG. 2 is a perspective view of a control unit for a patient support positioned on a footboard portion of an exemplary hospital bed, with a portion of the patient support being cut away to show interior components of the patient support.

FIG. 2 shows an illustrative embodiment of a patient support or mattress 10 having automated features in accordance with the present invention. Patient support 10 can accommodate a patient of any size, weight, height or width. It is also within the scope of the present invention to accommodate bariatric patients of up to 1000 pounds or more. To accommodate patients of varied sizes, the patient support may include a width of up to 50 inches or more.

Patient support 10 is positioned on or supported by an exemplary bed 2. Bed 2, as illustrated, is a hospital bed including a frame 4, a headboard 36, a footboard 38, and a plurality of siderails 40.

Frame 4 of the exemplary bed 2 generally includes a deck 6 supported by a base 8. Deck 6 includes one or more deck sections (not shown), some or all of which may be articulating sections, i.e., pivotable with respect to base 8. In general, patient support 10 is configured to be supported by deck 6.

Patient support 10 has an associated control unit 42, which controls automated features of patient support 10, such as inflation and deflation of internal components of patient support 10. Control unit 42 includes a user interface 44, which enables caregivers, service technicians, and/or service providers to configure patient support 10 according to the needs of a particular patient. For example, support characteristics of patient support 10 may be adjusted according to the size, weight, position, or activity level of the patient. User interface 44 is password-protected or otherwise designed to prevent access by unauthorized persons.

User interface 44 also enables patient support 10 to be adapted to different bed configurations. For example, deck 6 may be a flat deck or a step or recessed deck. An end user may select the appropriate deck configuration via user interface 44. Inflation or deflation of specific mattress components may occur in response to user selection of a hospital bed frame or deck configuration.

Figure 3:
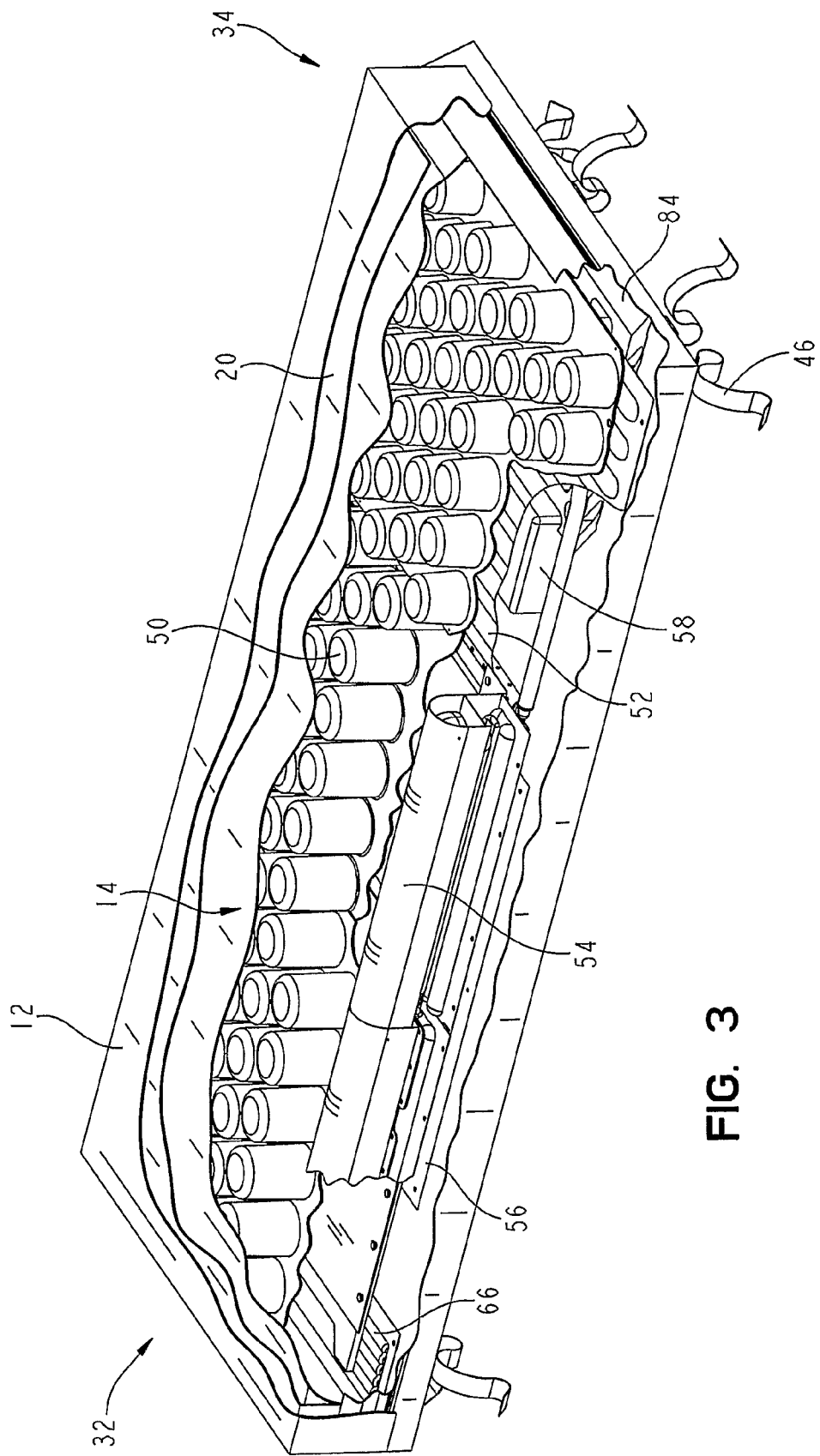
FIG. 3 is a perspective view of the exemplary patient support, with a portion being cut away to show interior components of the patient support.

Referring now to FIG. 3, patient support 10 has a head end 32 generally configured to support a patient's head and/or upper body region, and a foot end 34 generally configured to support a patient's feet and/or lower body region. Patient support 10 includes a cover 12 which defines an interior region 14. In the illustrated embodiment, interior region 14 includes a first layer 20, a second layer 50, and a third layer 52. Other embodiments of the present invention may not include all three of these layers, or may include additional layers.

In the illustrated embodiment, first layer 20 includes a support material, second layer 50 includes a plurality of vertically-oriented inflatable bladders located underneath the first layer 20, and third layer 52 includes a plurality of pressure sensors located underneath the vertical bladders of second layer 50.

Also located within interior region 14 of the exemplary patient support are a plurality of bolsters 54, one or more filler portions 56, and a pneumatic valve control box 58. A fire-resistant material (not shown) may also be included in the interior region 14.

Patient support 10 may be coupled to deck 6 by one or more couplers 46. Illustratively, couplers 46 are conventional woven or knit or fabric straps including a D-ring or hook and loop assembly or Velcro®-brand strip or similar fastener. Other suitable couplers, such as buttons, snaps, or tethers may also be used.

Figure 4:
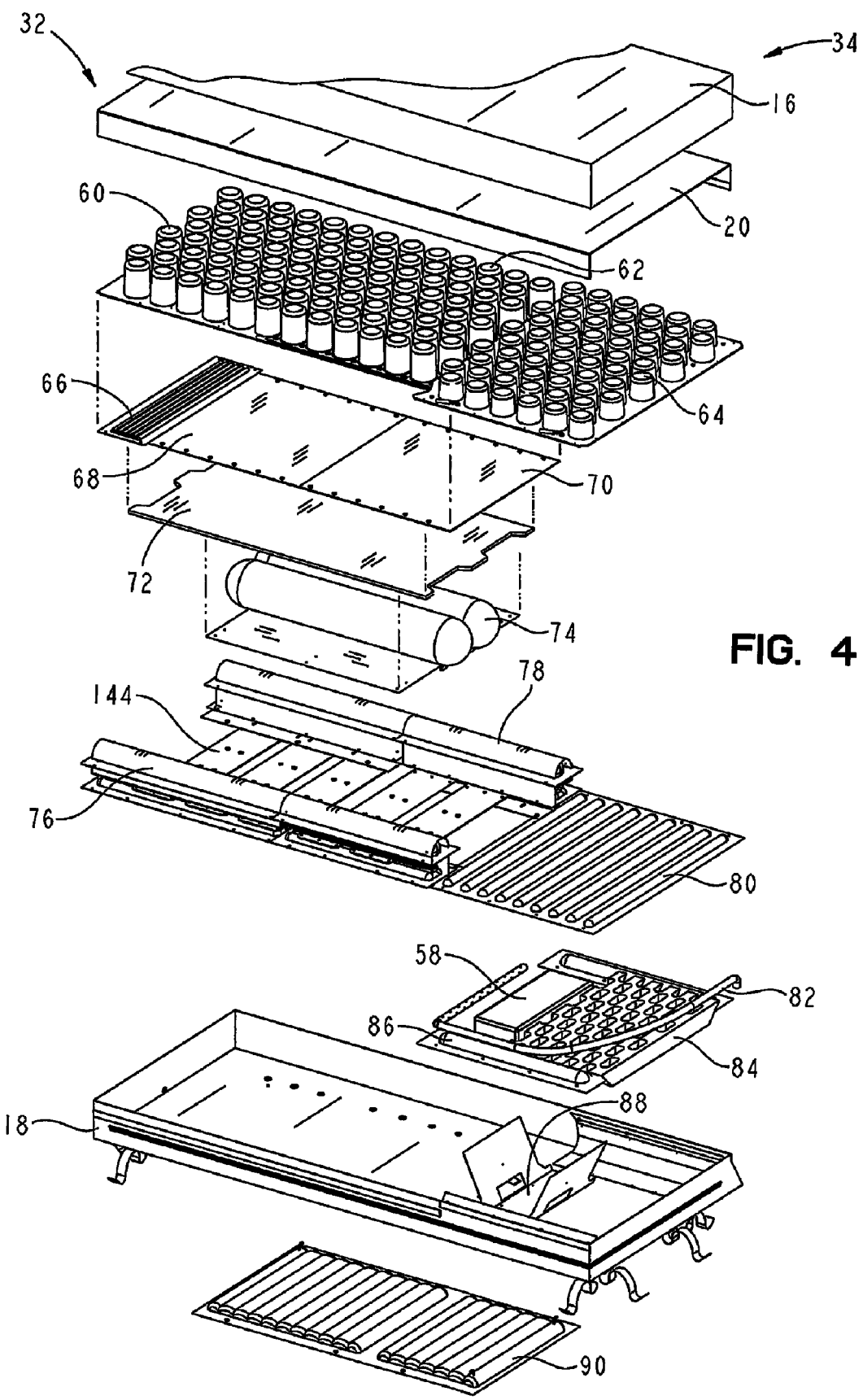
FIG. 4 is an exploded view of components of the exemplary patient support.

Components of the illustrated embodiment of a patient support in accordance with the present invention are shown in exploded view in FIG. 4. This embodiment of patient support 10 includes a top cover portion 16 and a bottom cover portion 18. Top cover portion 16 and bottom cover portion 18 couple together by conventional means (such as zipper, Velcro® strips, snaps, buttons, or other suitable fastener) to form cover 12, which defines interior region 14. While a plurality of layers, features, and/or components are illustrated within interior region 14, neither the illustrated embodiment of patient support 10 nor the present invention requires all of the illustrated components to be present.

A first support layer 20 is located below top cover portion 16 in interior region 14. First support layer 20 includes one or more materials, structures, or fabrics suitable for supporting a patient, such as foam, inflatable bladders, or three-dimensional material. Suitable three-dimensional materials include Spacenet, Tytex, and/or similar materials.

Returning to FIG. 4, a second support layer 50 including one or more inflatable bladder assemblies, is located underneath the first support layer 20. The illustrated embodiment of the second support layer 50 includes first, second and third bladder assemblies, namely, a head section bladder assembly 60, a seat section bladder assembly 62, and a foot section bladder assembly 64. Other embodiments include only one bladder assembly extending from head end 32 to foot end 34, and other arrangements of multiple bladder assemblies, for example, including an additional thigh section bladder assembly. In general, bladder assemblies disclosed herein are formed from a lightweight, flexible air-impermeable material such as a polymeric material like polyurethane, urethane-coated fabric, vinyl, or rubber.

A pressure-sensing layer 69 illustratively including first and second sensor pads, namely a head sensor pad 68 and a seat sensor pad 70, is positioned underneath bladder assemblies 60, 62, 64. Head sensor pad 68 is generally aligned underneath head section bladder assembly 60, and seat sensor pad 70 is generally aligned underneath seat section bladder assembly 62, as shown. Head filler 66 may be positioned adjacent head sensor pad 68 near head end 32 so as to properly position head sensor pad 68 underneath the region of patient support 10 most likely to support the head or upper body section of the patient. In other embodiments, a single sensor pad or additional sensor pads, for example, located underneath foot section bladder assembly 64, and/or different alignments of the sensor pads, are provided.

In the illustrated embodiment, a turn-assist cushion or turning bladder or rotational bladder 74 is located below sensor pads 68, 70. The exemplary turn-assist cushion 74 shown in FIG. 4 includes a pair of inflatable bladders 74a, 74b. Another suitable rotational bladder 74 is a bellows-shaped bladder. Another suitable turn-assist cushion is disclosed in, for example, U.S. Pat. No. 6,499,167 to Ellis, et al., which patent is owned by the assignee of the present invention and incorporated herein by this reference.

A plurality of other support components 66, 72, 76, 78, 80, 84, 86, 90 are also provided in the mattress of FIG. 4. One or more of these support components are provided to enable patient support 10 to be used in connection with a variety of different bed frames, in particular, a variety of bed frames having different deck configurations. One or more of these support components may be selectively inflated or deflated or added to or removed from patient support 10 in order to conform patient support 10 to a particular deck configuration, such as a step or recessed deck or a flat deck.

The support components illustrated in FIG. 4 are made of foam, inflatable bladders, three-dimensional material, other suitable support material, or a combination of these. For example, as illustrated, head filler 66 includes a plurality of foam ribs extending transversely across patient support 10. Head filler 66 could also be an inflatable bladder. Filler portion 72 includes a foam layer positioned substantially underneath the sensor pads 68, 70 and extending transversely across the patient support 10. In the illustrated embodiment, filler portion 72 includes a very firm foam, such as polyethylene closed-cell foam, with a ½-inch thickness.

Head bolster assembly 76, seat bolster assembly 78, and foot section bolster assembly 86 each include longitudinally-oriented inflatable bladders spaced apart by coupler plates 144.

As illustrated, first foot filler portion 80 includes a plurality of inflatable bladders extending transversely across patient support 10, and second foot filler portion 84 includes a foam member, illustratively with portions cut out to allow for retractability of the foot section or for other reasons. Deck filler portion 90 includes a plurality of transversely-extending inflatable bladders. As illustrated, deck filler portion 90 includes two bladder sections located beneath the head and seat sections of the mattress, respectively, and is located outside of cover 12. Deck filler portion 90 may include one or more bladder regions, or may be located within interior region 14, without departing from the scope of the present invention.

Also provided in the illustrated embodiment are a pneumatic valve box 58 and an air supply tube assembly 82. Receptacle 88 is sized to house pneumatic valve box 58. In the illustrated embodiment, receptacle 88 is coupled to bottom cover portion 18 by Velcro® strips. Pneumatic box 58 and tube assembly 82 are described below with reference to FIG. 5, and FIGS. 8-9.

In the illustrated embodiment, support layer 20 includes a breathable or air permeable material which provides cushioning or support for a patient positioned thereon and allows for circulation of air underneath a patient. The circulated air may be at ambient temperature, or may be cooled or warmed in order to achieve desired therapeutic effects.

Also in the illustrated embodiment, support layer 20 includes or is enclosed in a low friction air permeable material (such as spandex, nylon, or similar material) enclosure that allows support layer 20 to move with movement of a patient on patient support 10, in order to reduce shear forces, for instance. In other embodiments, the enclosure is made of a non-air permeable, moisture/vapor permeable material such as Teflon or urethane-coated fabric.

Figure 5:
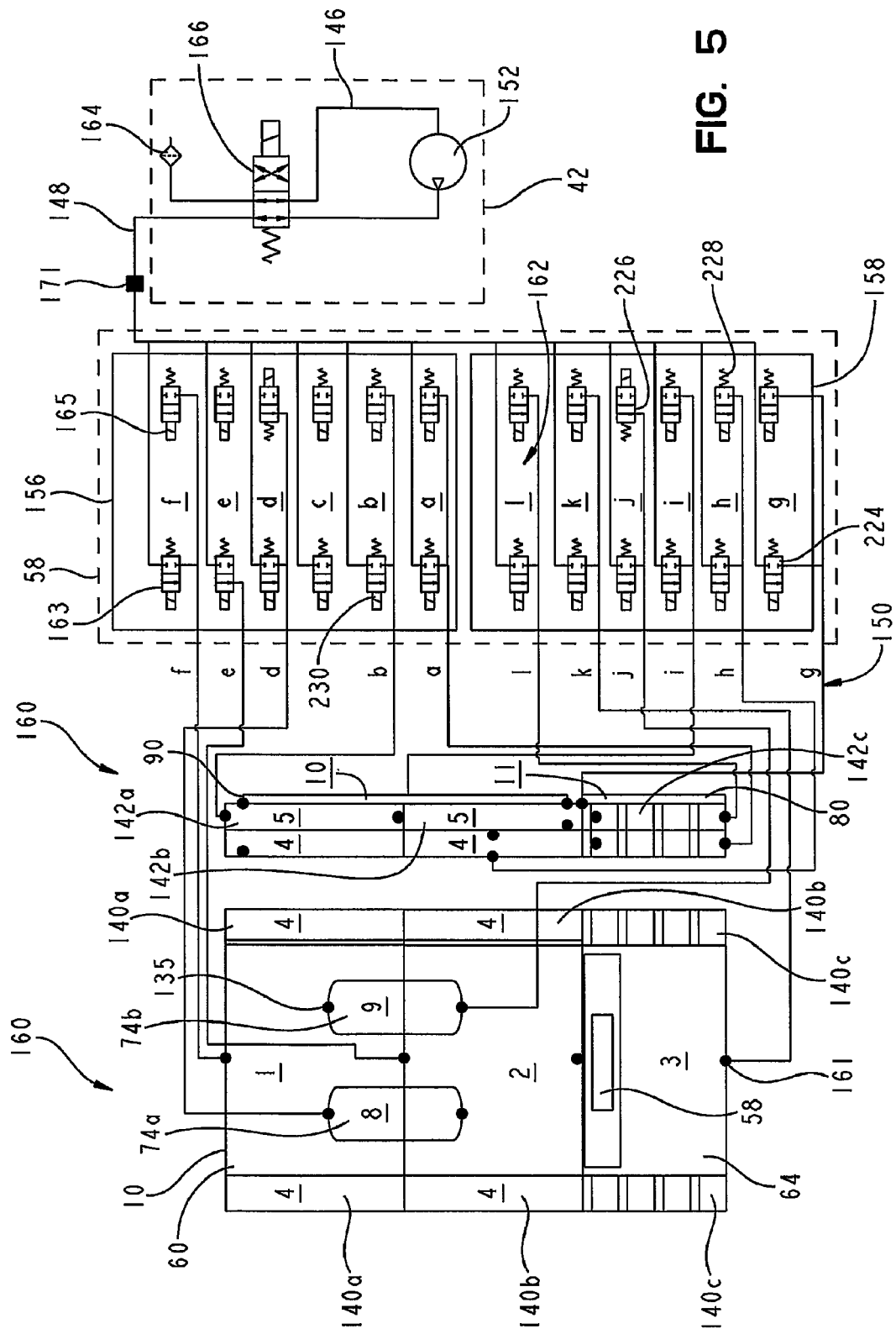
FIG. 5 is a schematic view of air zones of the exemplary patient support and couplings to a control unit.

A schematic diagram of the pneumatic control system of patient support 10 is shown in FIG. 5. Reading FIG. 5 from left to right, there is shown a simplified top view of patient support 10 with portions removed to better illustrate the various air zones 160, a simplified side view of patient support 10, a schematic representation of pneumatic valve box 58, a schematic representation of control unit 42, and air lines 146, 148, 150 linking control unit 42, valve box 58, and air zones 160.

As shown in FIG. 5, air zones 160 of patient support 10 are assigned as follows: zone 1 corresponds to head section bladder assembly 60, zone 2 corresponds to seat section bladder assembly 62, zone 3 corresponds to foot section bladder assembly 64, zone 4 corresponds to upper side bolsters 140, zone 5 corresponds to lower side bolsters 142, zone 6 corresponds to upper foot bolsters 140, zone 7 corresponds to lower foot bolsters 142, zone 8 corresponds to first turn-assist bladder 74, zone 9 corresponds to second turn-assist bladder 74, zone 10 corresponds to deck filler 90, and zone 11 corresponds to foot filler 80.

An air line 150 couples each zone 160 to a valve assembly 162 in valve box 58. Valve box 58 is located in the foot section 34 of patient support 10. Illustratively, valve box 58 is releasably coupled to bottom portion 18 of cover 12 in interior region 14, i.e., by one or more Velcro®-brand fasteners or other suitable coupler.

Each air line 150 is coupled at one end to an inlet port 135 on the corresponding bladder or bladder assembly. Each air line 150 is coupled at its other end to a valve assembly 162. Each valve assembly 162 includes first or fill valve 163 and a second or vent valve 165. First valves 163 are coupled to air supply 152 of control unit 42 by air lines 148. First valves 163 thereby operate to control inflation of the corresponding zone 160 i.e. to fill the zone with air. Second valves 165 operate to at least partially deflate or vent the corresponding zone 160, for example, if the internal air pressure of the zone 160 exceeds a predetermined maximum, or if deflation is necessary or desirable in other circumstances (such as a medical emergency, or for transport of patient support 10).

Each valve 163, 165 has an open mode 224 and a closed mode 226, and a switching mechanism 228 (such as a spring) that switches the value from one mode to another based on control signals from control unit 42. In closed mode 226, air flows from air supply 152 through the value 163 to the respective zone 160 to inflate the corresponding bladders, or in the case of vent valves 165, from the zone 160 to atmosphere. In open mode 224, no inflation or deflation occurs.

In the illustrated embodiment, an emergency vent valve 230 is provided to enable quick deflation of turning bladders 74 which draws air from atmosphere through a filter 164 and also vents air to atmosphere through filter 164. Air supply 152 is an air pump, compressor, blower, or other suitable air source.

Air supply 152 is coupled to a switch valve 166 by air line 146. Switch valve 166 operates to control whether inflation or deflation of a zone occurs. An optional proportional valve 171 may be coupled to air line 148 to facilitate smooth inflation or deflation of turn-assist bladders 74, or for other reasons.

In the illustrated embodiment, valve box 58 includes a first valve module 156 and a second valve module 158. First valve module 156 includes valves generally associated with a patient's first side and second valve module 158 includes valves generally associated with a patient's second side.

The various zones 160 are separately inflatable. Certain of the zones 160 are inflated or deflated to allow patient support 10 to conform to different bed frame configurations. For example, the deck filler 90 (zone 10 in FIG. 5) is inflated to conform patient support 10 to certain bed frame configurations, such as step deck configurations including the Total-Care® and CareAssist® bed frames, made by Hill-Rom, Inc., the assignee of the present invention, but is deflated when patient support 10 is used with a flat deck bed frame, such as the Advanta® bed made by Hill-Rom, Inc. As another example, the foot filler 80 (zone 11 in FIG. 5) is inflated when patient support 10 is used with the VersaCare®, TotalCare®, or CareAssist® beds, but the lower side bolsters 142 (zone 5 in FIG. 5) are not inflated when patient support 10 is used with a VersaCare® bed. As still another example, the lower foot bolsters 142 (zone 7 in FIG. 5) are inflated when patient support 10 is used on flat decks or other bed frames, including the Advanta® and VersaCare® bed frames made by Hill-Rom, Inc.

Figure 6:
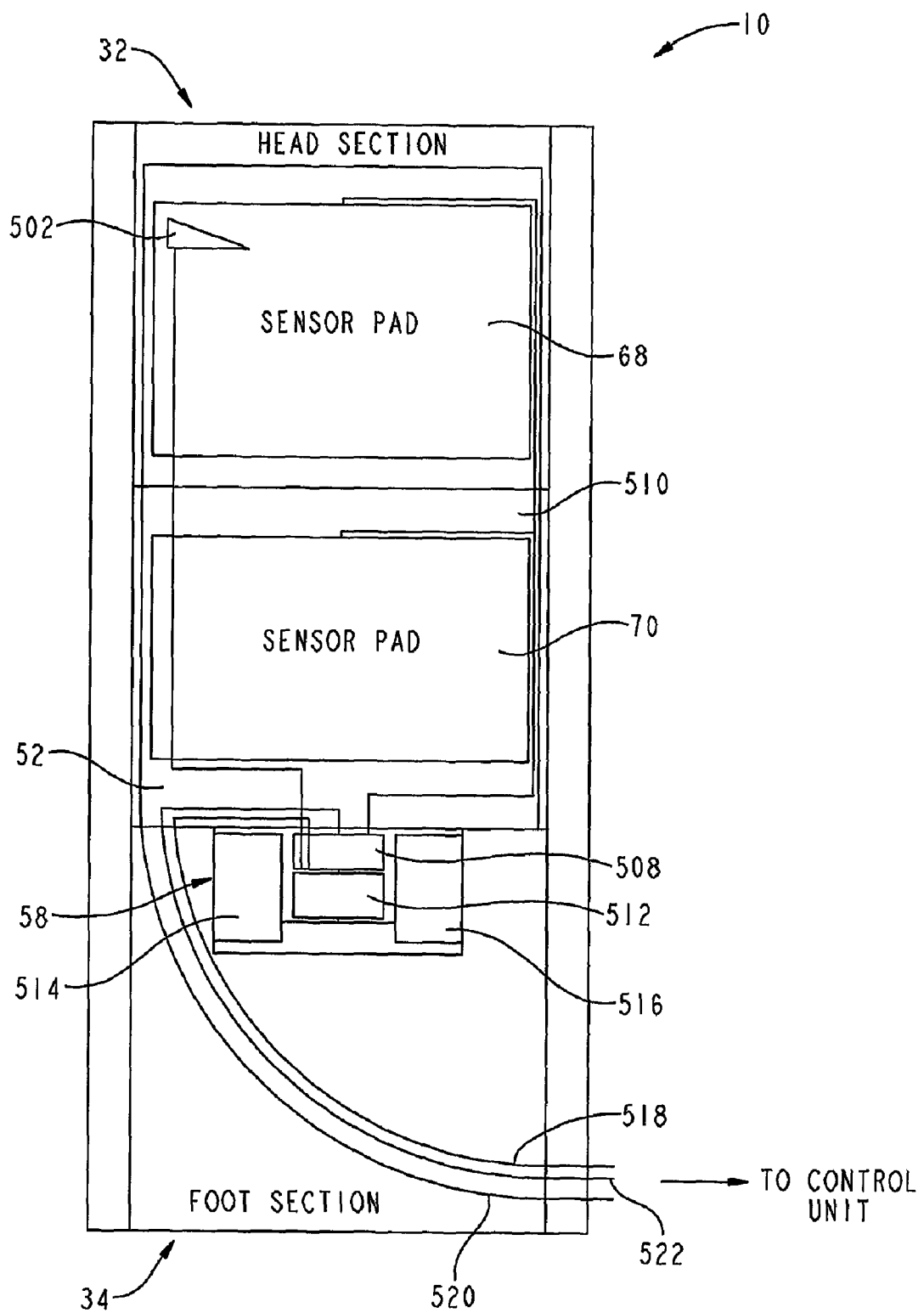
FIGS. 6 and 7 are schematic diagrams of portions of a control system for the exemplary patient support.
Figure 7:
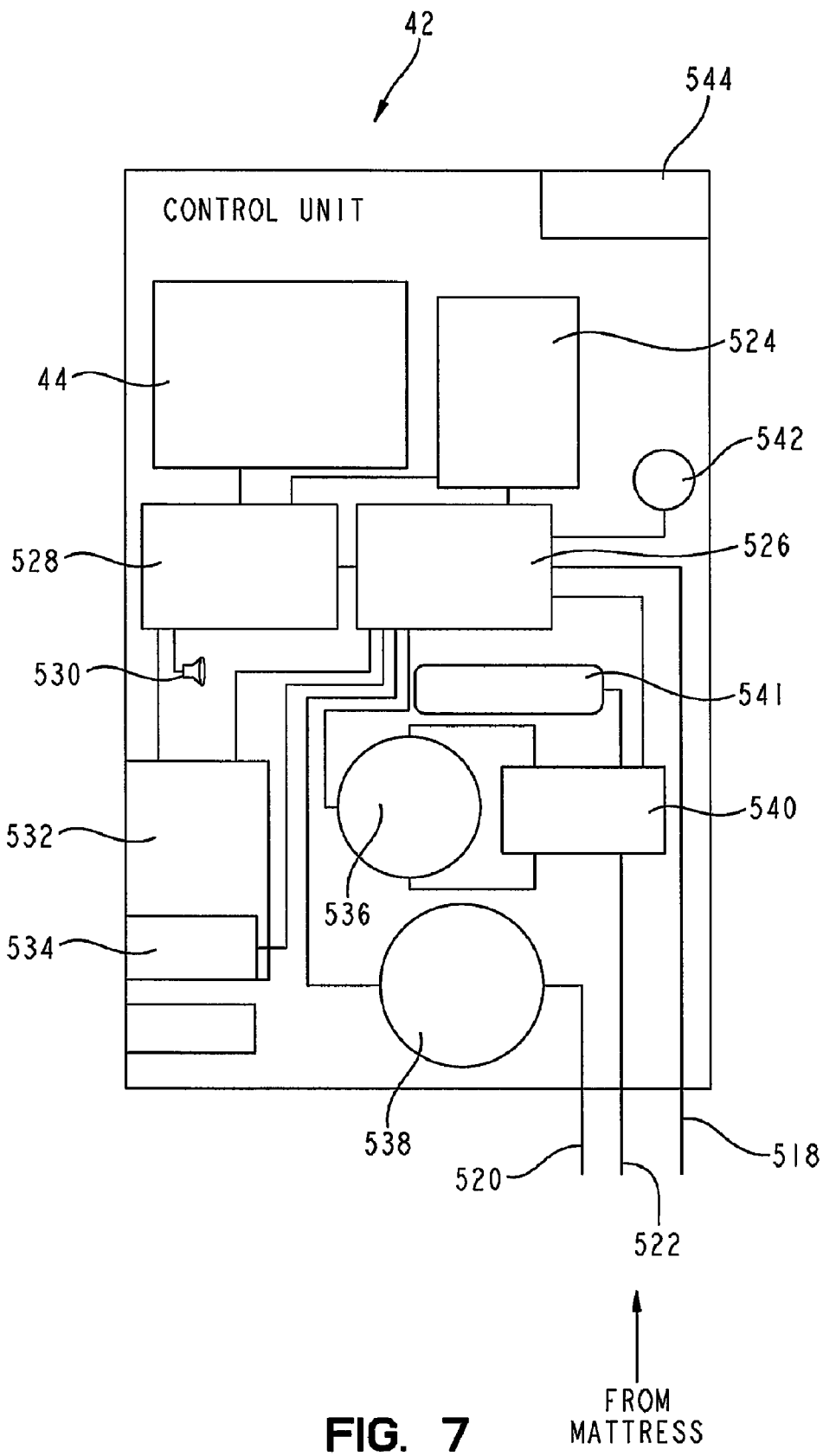

FIGS. 6 and 7 are a simplified schematic diagram of a control system for a patient support or mattress 10 in accordance with the present invention. FIG. 6 schematically illustrates the patient support 10 including the various components of patient support 10 whereas FIG. 7 schematically illustrates the control unit 42 and various components therein. The patient support 10 includes the sensor pad 52 which is coupled to the pneumatic valve control box 58 as previously described. The sensor pad 52 includes a head sensor pad 68 and a seat sensor pad 70. The head sensor pad 68 is located at the head end 32 of the mattress 10. The seat sensor pad 70 is located at a middle portion of the mattress 10 which is located between the head end 32 and a location of the pneumatic valve control box 58. The seat sensor pad 70 is located such that a patient laying upon the mattress 10 may have its middle portion or seat portion located thereon when in a reclined state. In addition, when the head end 32 of the mattress 10 is elevated, the seat portion of the patient is located above the seat sensor pad 70. The head sensor pad 68 is located beneath the head section bladder assembly 60 and the seat sensor pad 70 is located beneath the seat section bladder assembly 62. Each one of the sensors of the head sensor pad 68 or the seat sensor pad 70 is located beneath or at least adjacent to one of the upstanding cylindrical bladders or cushions 50. A head angle sensor 502 is coupled to the control box 58 where signals received from the sensor may provide head angle information and pressure adjustment information for adjusting pressure in the seat bladders 62.

The sensor pad 52 is coupled through the associated cabling to the pneumatic control box 58. The pneumatic control box 58 includes a multiplexer 508 coupled to the head sensor pad 68 and the seat sensor pad 70 through a signal and control line 510. The multiplexer board 508 is also coupled to an air control board 512 which is in turn coupled to a first valve block 514 and a second valve block 516. A communication/power line 518 is coupled to the control unit 42 of FIG. 7. Likewise, a ventilation supply line 520 which provides for air flow through the patient support 10 for cooling as well as removing moisture from the patient is also coupled to the control unit 42 of FIG. 7. An air pressure/vacuum supply line 522 for inflating or deflating air bladders is coupled to the control unit 42 as well.

The control unit 42 of FIG. 7 includes the display 44, which displays user interface screens, and a user interface input device 524 for inputting to the control unit 42 user selectable information, such as the selection of various functions or features of the present device. The selections made on the user interface input device 524 control various aspects of the operation of the patient support 10, which can include selectable pressure control of various bladders within the mattress 10, control of the deck 6, for instance to put the bed 2 in a head elevated position, as well as displaying the current state of the mattress or deck position, and other features.

An algorithm control board 526 is coupled to the user interface input device 524. The algorithm control board 526 receives user generated input signals received through the input device 524 upon the selection of such functions by the user. The input device 524 can include a variety of input devices, such as pressure activated push buttons, a touchscreen, as well as voice activated or other device selectable inputs. The algorithm control board 526 upon receipt of the various control signals through the user input device 524 controls not only the operation of the mattress 10 but also a variety of other devices which are incorporated into the control unit 42. For instance, the algorithm control board 526 is coupled to a display board 528 which sends signals to the display 44 to which it is coupled. The display board 528 is also connected to an output device, e.g., a speaker 530, which generates audible signals which might indicate the selection of various features at the input device 24 or indicate a status of a patient positioned on patient support (e.g. exiting) or indicate a status of therapy being provided to the patient (e.g., rotational therapy complete). The algorithm control board 526 receives the required power from power supply 532 which includes an AC input module 534, typically coupled to a wall outlet within a hospital room or other patient care or healthcare facility.

The algorithm control board 526 is coupled to an air supply, which, in the illustrated embodiment includes a compressor 536 and a blower 538. Both the compressor 536 and the blower 538 receive control signals generated by the algorithm control board 526. The compressor 536 is used to inflate the air bladders in accordance with instructions received from the algorithm control board 526. The blower 538 is used for air circulation which is provided through the ventilation supply line 520 to the mattress 10. It is, however, possible that the compressor 536 may be used to both inflate the bladders and to circulate the air within the mattress 10. A pressure/vacuum switch valve 540 is coupled to the compressor 536 which is switched to provide for the application of air pressure or a vacuum to the mattress 10. A muffler 541 is coupled to the valve 540. In the pressure position, air pressure is applied to all or a portion of the mattress 10 to inflate the mattress or portion thereof for support of the patient. In the vacuum position, the valve 540 is used to apply a vacuum to the bladders therein such that the mattress may be placed in a collapsed state for moving to another location or for providing a CPR function, for example. A CPR button 542 is coupled to the algorithm control board 526.

An identification tag 544 may also be associated with the control unit 42. The identification tag 544 may be affixed to an exterior surface of the control unit housing, or may be installed within the interior region of the control unit housing. The ID tag may include bar code, or magnetic strip, or may generate an infrared, radio frequency, or other suitable electromagnetic signal indicating a unique identifier associated with the control unit 42. Such unique identifier may be used to locate, track, or monitor the status of the control unit, for example, using a locating and tracking system. One example of such a locating and tracking system is disclosed in U.S. Pat. No. 6,462,656 to Ulrich, et al., assigned to the assignee of the present invention and incorporated herein by this reference.

As illustrated, the algorithm control board 526, the compressor 536, the blower 538, and the user input device or user control module 524 are located externally to the mattress and are a part of the control unit 42, which may be located or removably positioned on the footboard 38 as shown in FIG. 1. The sensors and sensor pad 52, the pneumatic valve control box 58, and the air control board or microprocessor 512 for controlling the valves and the sensor pad system 52 are located within the mattress 10. It is within the present scope of the invention to locate some of these devices within different sections of the overall system, for instance, such that the algorithm control board 526 could be located within the mattress 10 or the air control board 512 could be located within the control unit 42. Also, control box 58 could be combined with control unit 42 and be positioned outside the mattress 10.

Figure 8:
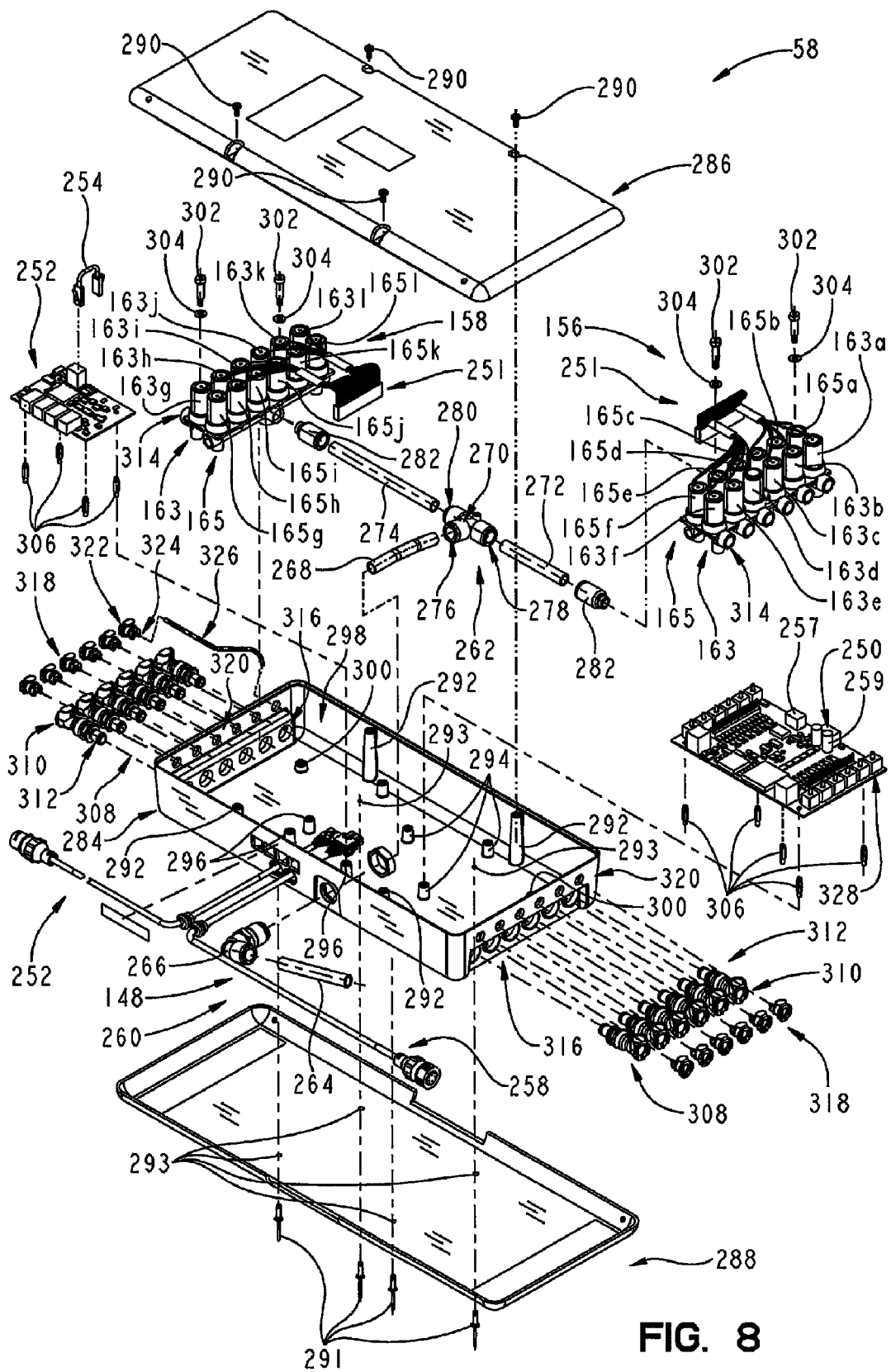
FIG. 8 is an exploded view of an exemplary pneumatic assembly.
Figure 9:
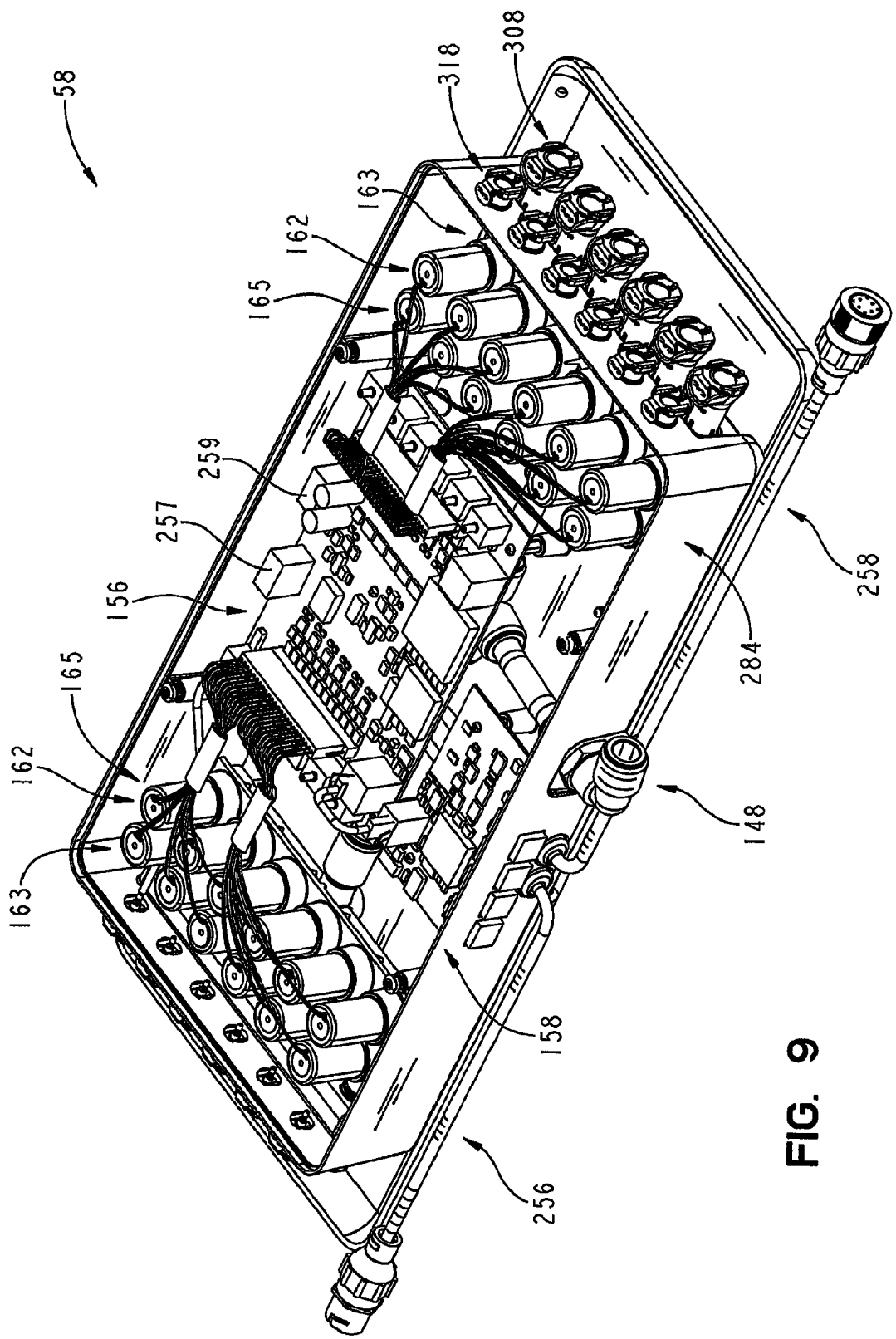
FIG. 9 is a perspective view of the pneumatic assembly of FIG. 8.

As shown in FIGS. 8-9, one embodiment of control box 58 includes a multiplexer 252 and an air control board 250. Control board 250 is coupled to multiplexer 252 by a jumper 254. Multiplexer 252 is further coupled to head sensor pad 68 and seat sensor pad 70 through a signal and control line (not shown). Control board 250 is also coupled to first valve module 156 and second valve module 158 by wire leads 251. A communication/power line 258 couples control board 250 to the control unit 42. Communication line 258 couples to a communication plug 259 of control board 250. Jumper 254 couples multiplexer 252 to control board 250 for power and access to communication line 258. Wire leads 251 provide actuation power to first and second valve modules 156, 158.

An angle sensor cable 256 is provided to send a signal from a head angle sensor 502 to the control board 250. Angle sensor cable 256 couples to an angle plug 257 of control board 250. In the illustrated embodiment, head angle sensor 502 is located within head bolster assembly 76. Head angle sensor 502 indicates the angle of elevation of the head end 32 of bed 2 as the head section of the frame 4 articulates upwardly raising the patient's head or downwardly lowering the patient's head. In one embodiment, angle sensor 502 transmits the angle of head end 32 to all nodes or circuit boards within the mattress control system 42, 58. Angle sensor 502 generates an indication or indicator signal when head end 32 is at an angle of at least 5°, at least 30°, and at least 45°. The head angle indication is transmitted to the control unit 42 which evaluates and processes the signal. When head end 32 is at an angle above 30° turn assist 74 becomes inoperative primarily for patient safety reasons. When head end 32 is at an angle above 45° information is transmitted to control unit 42 for use in the algorithms. The 5° angle indication is primarily to ensure relative flatness of patient support 10. In the illustrated embodiment, angle sensor 502 is a ball switch or string potentiometer.

As discussed above, first and second valve modules 156, 158 include fill valves 163 and vent valves 165. First valve module 156 includes fill valves 163a-f and vent valves 165a-f. Second valve module 156 includes fill valves 163g-l and vent valves 165g-l. Fill valves 163a-l and vent valves 165a-l are 12 Volt 7 Watt solenoid direct active poppet style valves in the illustrated embodiment. Control board 252 is able to actuate each fill valve 163a-l and vent valve 165a-l independently or simultaneously. Fill valves 163a-l and vent valves 165a-l are all able to be operated at the same time. In operation to initiate each valve 163, 165, control board 250 sends a signal to the valve to be operated. The signal causes a coil (not shown) within each valve to energize for ½ second and then switches to pulsate power (i.e., turn on and off at a high rate) to save power during activation. The activation in turn cause the valve to either open or close depending on which valve is initiated.

Fill valves 163 are coupled to air supply 152 of control unit 42 by second air line 148. Air line 148 includes an outer box line assembly 260 and an inner box line assembly 262. Outer box line assembly 260 includes an exterior inlet hose 264 and an elbow 266 coupled to exterior inlet hose 264. Inner box line assembly 262 includes an interior inlet hose 268 coupled to elbow 266, a union tee connector 270, a first module hose 272, and a second module hose 274. Connector 270 includes a first opening 276 to receive interior inlet hose 268, a second opening 278 to receive first module hose 272, and a third opening 280 to receive second module hose 274. First and second module hoses 272, 274 each couple through a male coupler 282 to first and second valve modules 156, 158 respectively. In operation, air from air supply 152 travels through supply line 148, enters outer box line assembly 260 through exterior inlet hose 264 and passes through elbow 266 to interior inlet hose 268. The air then travels from inlet hose 268 to union tee connector 270 where the air is divided into first module hose 272 and second module hose 274. The air passes through first and second module hoses 272, 274 into first and second valve modules 156, 158 respectively. The operation of first and second valve modules 156, 158 is described below.

Control box 58 includes a base 284, a cover 286, and a tray 288. Cover 286 includes a plurality of fasteners (i.e., screws) 290. Base 284 includes a plurality of threaded cover posts 292. Cover posts 292 are configured to receive screws 290 to couple cover 286 to base 284. Cover 286 and base 284 define an inner region 298. Tray 288 couples to base 284 with a plurality of rivets 291 riveted through a plurality of rivet holes 293 located on tray 288 and base 284.

Inner box line assembly 262, first valve module 156, second valve module 158, control board 250, and multiplexer 252 are contained within inner region 298. Base 284 further includes a plurality of control board posts 294, a plurality of multiplexer posts 296, and a plurality of module posts 300. First and second valve modules 156, 158 are coupled to module posts 300 by shoulder screws 302 and washers 304. Control board 250 and multiplexer 252 are respectively coupled to control board posts 294 and multiplexer posts 296 by a plurality of snap mounts 306.

First and second valve modules 156, 158 attach to third air lines 150 a, b, d-f, and g-l through a plurality of couplers 308. Couplers 308 include a first end 310 and a second end 312. Third air lines 150 a, b, d-f, and g-l each include a fitting (not shown) receivable by second end 312. Each first end 310 mounts to a port 314 in first and second valve modules 156, 158. First end 310 mounts through a plurality of openings 316 in base 284.

A plurality of feedback couplers 318 mount through a plurality of feedback openings 320 in base 284. Feedback couplers 318 include a first feedback end 322 and a second feedback end 324. First feedback end 322 couples to a feedback line (not shown) that in turn couples to a feedback port 135 located on each air zone 160. Second feedback end 324 receives a feedback transfer line 326. Each transfer line 326 couples to a pressure transducer 328 located on the control board 250. Pressure transducer 328 receives the pressure from each air zone 160 and transmits to control unit 42 a pressure data signal representing the internal air pressure of the zone 160. Control unit 42 uses these pressure signals to determine the appropriate pressures for certain mattress functions such as CPR, patient transfer, and max-inflate. Pressure signals from the transducer 328 coupled to the foot zone 160k are also used to maintain optimal pressure in foot zone 160k.

In the illustrated embodiment, pressure in foot zone 160k (zone 3) is computed as a percentage of the pressure in seat zone 160e (zone 2). The pressures in seat zone 160e and head zone 160f are determined using both the transducers 328 and the pressure sensors 136. The pressures in one or more of the zones 160 may be adjusted in real time.

As shown in FIG. 5, fill valves 163a-l and vent valves 165a-l are coupled to various portions of patient support 10 through third air lines 150 a, b, d-f, and g-l. Fill valve 163a and vent valve 165a are coupled to upper foot bolsters 140c, fill valve 163b and vent valve 165b are coupled to lower side bolsters 142 a, b, fill valve 163c is coupled to atmosphere and vent valve 165c is reserved for future therapies. Also, fill valve 163d and vent valve 165d are coupled to first turn assist 74a, fill valve 163e and vent valve 165e are coupled to seat bladders 62, fill valve 163f and vent valve 165f are coupled to head bladder assembly 60, fill valve 163g and vent valve 165g are coupled to foot filler 80, fill valve 163h and vent valve 165h are coupled to upper side bolsters 140 a, b, fill valve 163i and vent valve 165i are coupled to deck filler 90, fill valve 163j and vent valve 165j are coupled to first turn assist 74b, fill valve 163k and vent valve 165k are coupled to foot bladders 164, fill valve 163l and vent valve 165l are coupled to lower foot bolsters 142c. Vent valves 165d, j are biased in the open position to vent air from first and second turn assist 74a, 74b when first and second turn assist 74a, 74b are not in use. Vent valves 165d, j return to their open position if the mattress loses power or pressure venting air from the first and second turn assist 74a, 74b. When air is vented from a zone 160, the pressure in the zone 160 after deflation is determined by the control system 42, 58 in real time rather than being predetermined.

In one embodiment, a user enters an input command to control unit 42. Control unit 42 processes the input command and transmits a control signal based on the input command through communication line 258 to control board 250. Additionally or alternatively, control signals could be based on operational information from control unit 42 to increase or decrease pressure within one or more of the zones 160 based on information obtained from transducers 328 and/or sensors 136.

It should be noted that in the illustrated embodiment, the mattress controls 42, 58 are independent from operation of the bed frame 4. In other embodiments, however, bed frame 4 and mattress 10 may be configured to exchange or share data through communication lines. For instance, data may be communicated from bed frame 4 to mattress system 42, 58 and used to adjust support parameters of mattress 10. For instance, in one embodiment, a signal is transmitted from frame 4 when foot section 34 is retracting, so that mattress systems 42, 58 responds by decreasing internal pressure of vertical bladders 50 in foot assembly 64.

As described above, air supply 152 is capable of supplying air or acting as a vacuum to remove air from zones 160. While in supply mode, a microprocessor on control board 250 actuates corresponding fill valve 163a-l or vent valve 165a-l based on the control signal from control unit 42. For example, if the control signal indicates the pressure in head bladder assembly 160 is to be increased fill valve 163f is actuated. However, if the control signal indicates the pressure in head bladder assembly 160 is to be decreased vent valve 165f is actuated. While in vacuum mode one or more fill valves 163a-l may be actuated to allow for rapid removal of air within the corresponding zones.

Figure 10:
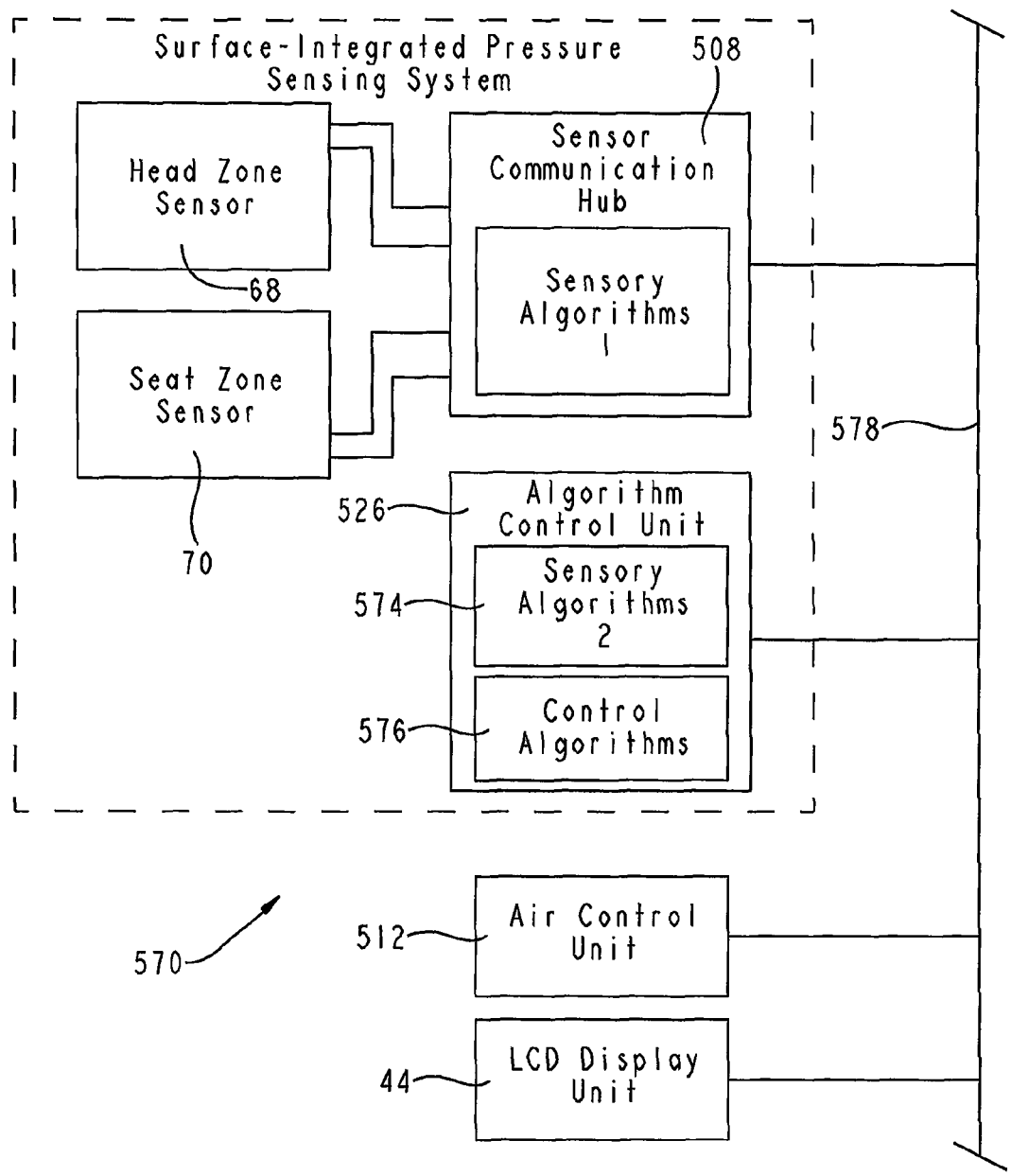
FIG. 10 illustrates a functional block diagram illustrating the head zone and seat zone sensors and other system components coupled to a communication network.

FIG. 10 illustrates an overall system architecture 570 of a mattress in accordance with the present invention. As previously described, the multiplexer board 508, also known as a sensor communication hub, is coupled to the head zone sensor 68 and the seat zone sensor 70. The multiplexer 508 as well as the optical system devices includes a number of sensory algorithms to be described later herein. Also included in the system architecture 570 is the algorithm control unit 526 which includes a second set of sensory algorithms 574 and control algorithms 576. The output of the multiplexer 508 and the algorithm control unit 526 are coupled to a network 578 which is also coupled to the air control unit 512 and the LCD display unit 44. The network 578 includes interface hardware, also known as a communication hub. The network 578 acts as the communication bus for the various hardware, software, and firmware control devices.

As previously described, the multiplexer 508 includes the sensory algorithms 572. The algorithm control unit 526 also includes sensory algorithms which may include algorithms for providing pressure relief, for providing a motion metric, for providing weight estimation, and for providing information to a LCD module which includes a calculation of statistics model.

Figure 11:
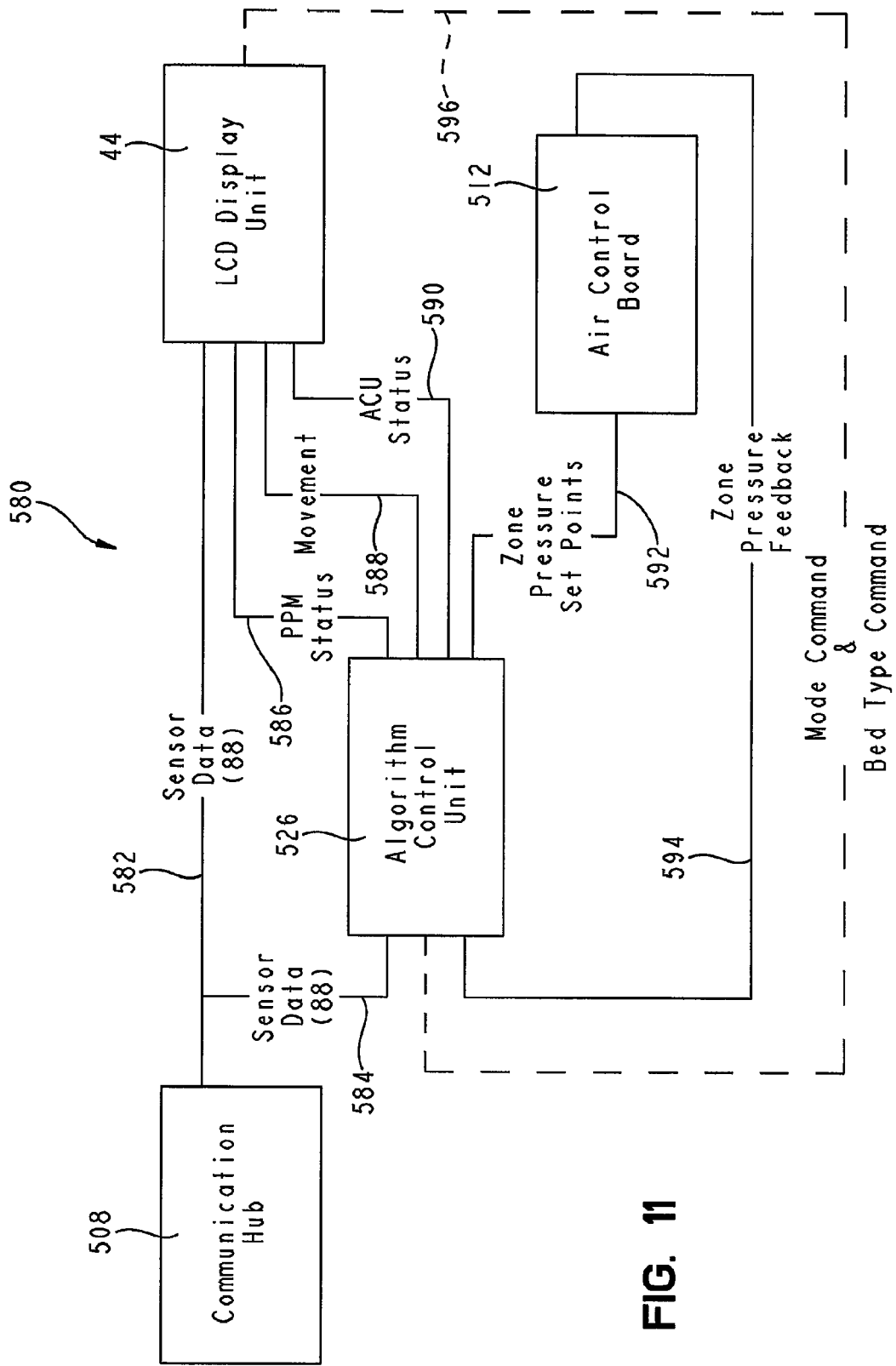
FIG. 11 illustrates a block diagram for a control system in accordance with the present invention including an algorithm control unit.

FIG. 11 illustrates a block diagram of a control system 580 incorporating the LCD display unit 44, the air control board 512, the communication hub or network 508, and the algorithm control unit 526. The communication hub 508 which receives sensor data from the head zone sensor 68 and the seat zone sensor 70 is coupled to both the LCD display unit 44 and the algorithm control unit 526 through a first sensor data line 582 and a second sensor data line 584 respectively. As described with respect to FIG. 10, the algorithm control unit 526 includes sensory algorithms 574 and control algorithms 576. The algorithm control unit 526 includes a first output line 586 coupled to the LCD display unit 44 for transmitting patient position monitor status, a second control line 588 for communicating movement status, and a third control line 590 for communicating the status of the algorithm control unit. In addition, the algorithm control unit 526 includes a fourth output line 592 which transmits the zone pressure boundary values for each of the head, seat and foot zones to the air control board 512 to which the line 592 is coupled. The air control board 512, which includes the pressure sensors previously described, sends control pressure zone feedback signals through a line 594 back to the algorithm control unit 526. The display unit 44 through the user input interface device 524 also sends control signals to the algorithm control unit 526 through a control line 596 which includes signals such as various mode command signals as well as bed type command signals for adjusting the frame or deck of the bed.

As previously described with reference to FIG. 10, the present invention includes sensory algorithms as well as control algorithms. The sensory algorithms are provided in firmware located within the multiplexer 508 and the algorithm control unit 526. Sensory algorithms include the following: bottom out detection, where a portion of the subject is supported by the bed frame as opposed to the surface, bed exit detection, sitting on the side of a bed detection, detection of a patient lying on the edge of the surface, detecting a lack of patient movement on the surface over a period of time, providing patient position monitoring by distinguishing between the following six positions left lying, left sitting, center lying, center sitting, right lying, right sitting, and measuring patient weight within plus or minus 20% within the bed and the flat position. The control system algorithms which are located in the control system algorithm firmware 576 optimize pressure reduction by dynamic load distribution adjustment of the surface air bladders of the mattress 10 located above the head sensor pad 68 and the seats sensor pad 70.

Figure 12:
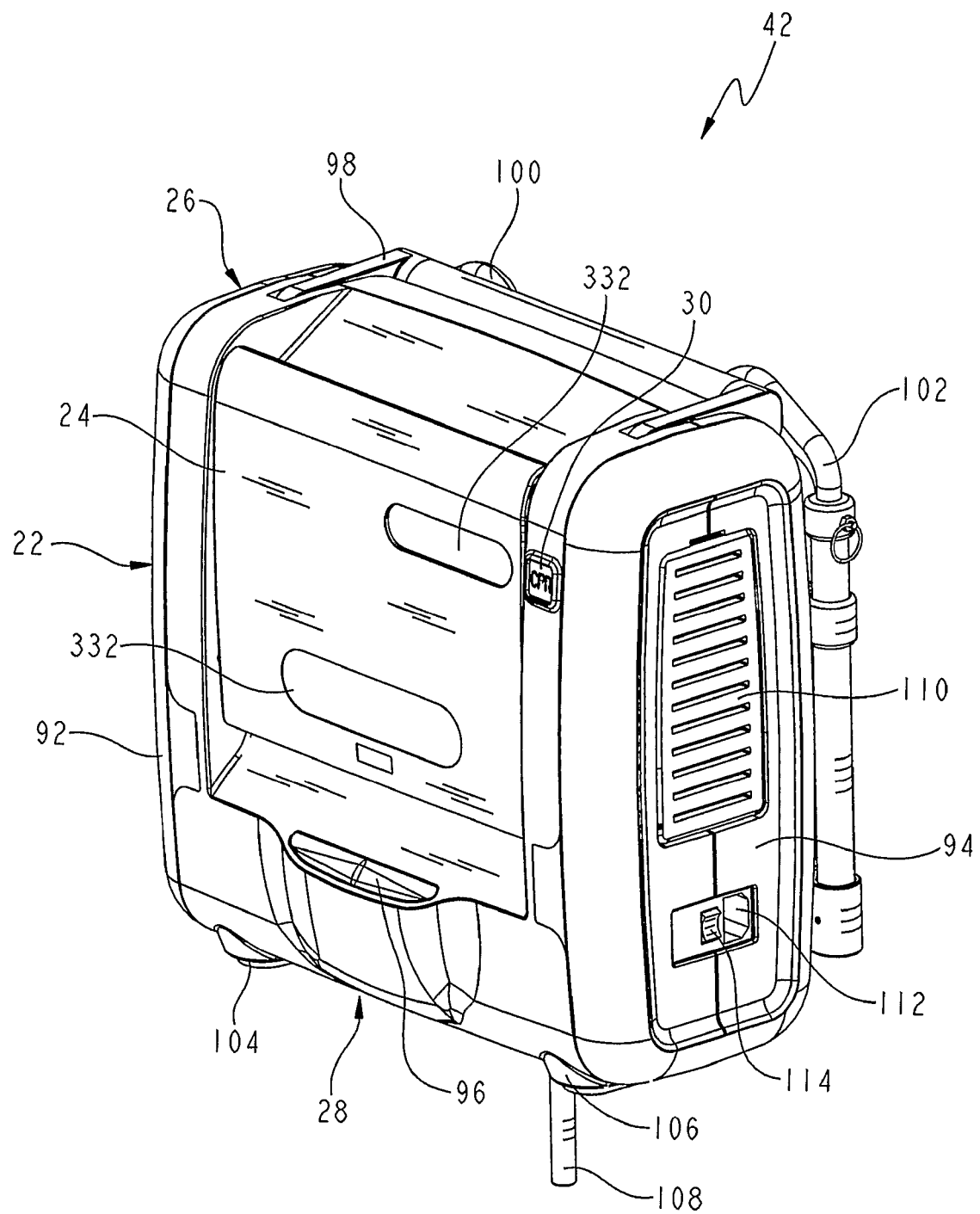
FIG. 12 is a perspective view of a control unit in accordance with the present invention.

Referring now to FIG. 12, the illustrated embodiment of the control unit 42 includes a housing 22. The exterior housing 22 includes a top end 26, a bottom end 28, a first side 92, and a second side 94. The exterior housing 22 defines an interior region containing control unit components to be described later herein.

A display portion 24 is pivotably coupled to the housing 22. Also shown coupled to the exterior housing 22 are a rotatable handle 98, a coupling assembly including first and second hangers 100, 102, an air filter 110, an electrical power input port 112, a power on/off switch 114, first and second feet 104, 106, and a cable 108. A visual indicator or light bar 96 is also provided.

Figure 13:
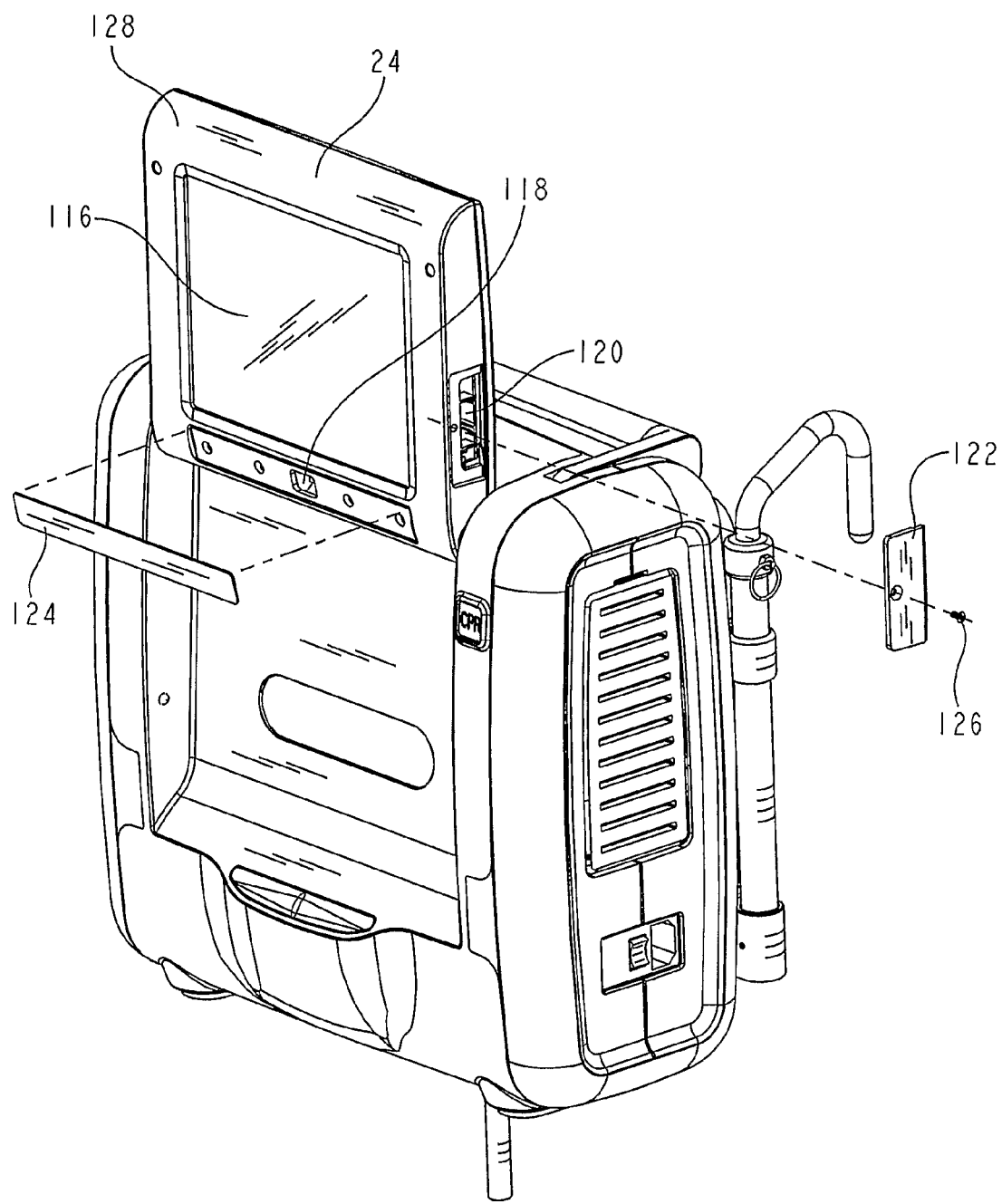
FIG. 13 is a perspective view of a control unit with a display portion rotated upward.

In FIG. 13, the display portion 24 is shown rotated upwardly into a use position. Once placed in a use position, the display panel 116 may be easily viewed by a caregiver. The display panel 116 is, in the illustrated embodiment, a liquid crystal display including a touchscreen control panel such that the user may simply touch the screen with a fingertip in designated areas to give instructions for controlling the patient support. As will be described later herein, the video display panel 116 is configured to be capable of displaying video clips and help screens, including videos that demonstrate operation, installation, and/or maintenance procedures for the patient support 10. All aspects of the user interface of display panel 116 are capable of being displayed in multiple languages, including, for example, English and Spanish. The display panel 116 is, in the illustrated embodiment an 8.4 inch high contrast mode flip up LCD display screen.

Also provided on display portion 24 is an infrared (IRDA) port 118, which enables data collection and/or communication over a network using wireless technology. For example, usage data regarding usage of the mattress 10, and/or service information (i.e. how often the mattress has been serviced) may be communicated to a remote computing device over a wireless network through the use of the infrared port 118.

A memory port 120 is also provided in the display portion 24. Memory port 120 is configured to removably receive memory cards such as compact flash memory, for example. SD memory cards, for example, may also be used, for example, in order to configure the control unit 42 with firmware upgrades, changes to the software, or updates or additional training or service videos. This eliminates the need to take the control unit 42 out of service in order to accomplish these and other types of upgrades and adjustments.

Also provided on display portion 24 are cover panels 122, 124, which are removably coupled to exterior housing 128 of the display portion 24. Cover panels 122, 124 are generally made of the same material as the rest of the exterior housing of display portion 24 (i.e., polycarbonate). Cover panels 122, 124 are provided primarily to protect the communication and data ports 118, 120 when those ports are not in use. Cover panels 122, 124 may be coupled to exterior housing 128 by one or more fasteners 126 (i.e., screws). Exterior housing 128 may also include a bracket configured to mate with a mating portion of a footboard, headboard, siderail or other similar port of a bed.

The usage data or service data that may be collected and transmitted through the infrared port 118 may include error logs or logs of the mattress usage.

Figure 14:
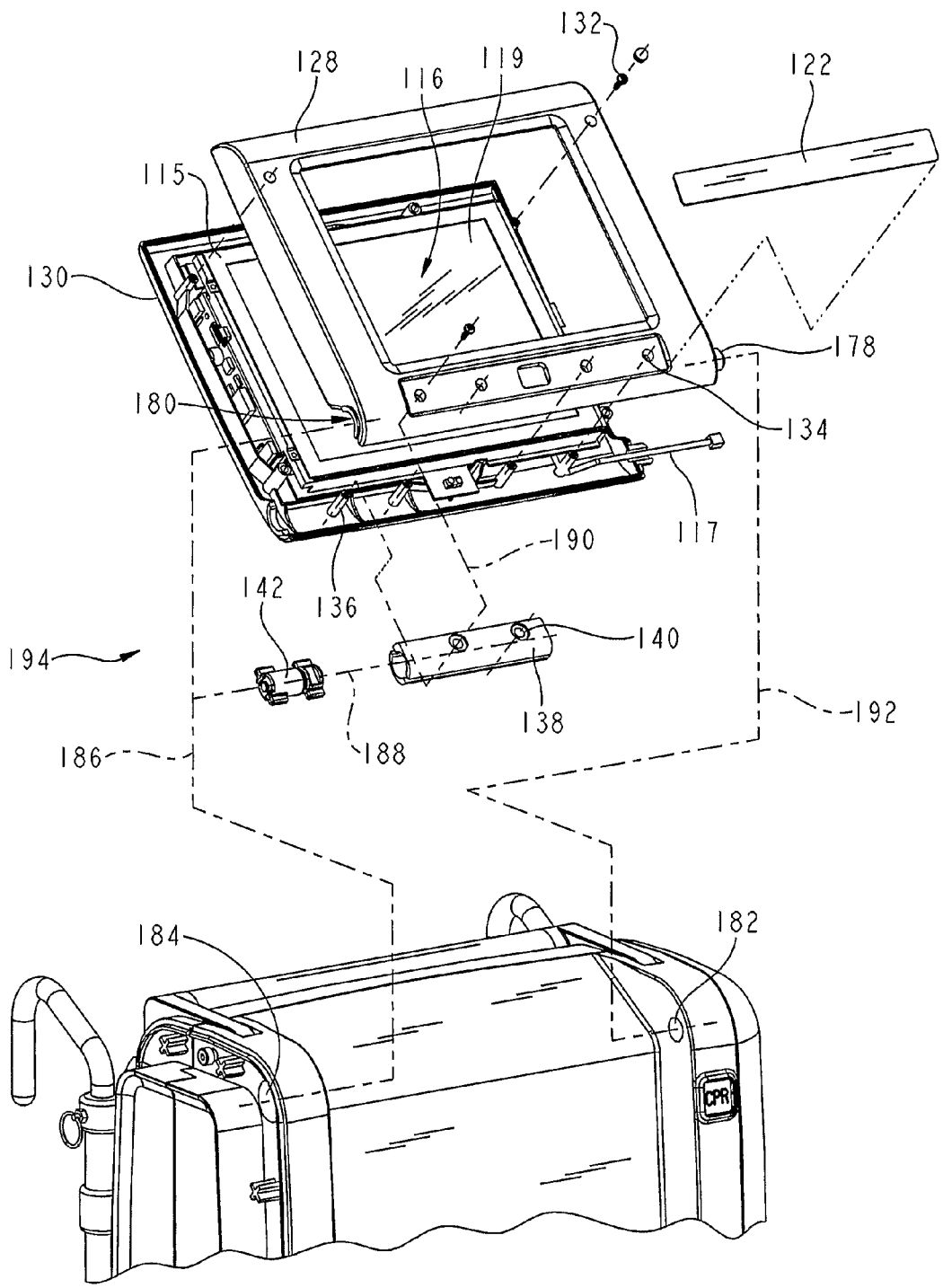
FIG. 14 is an exploded perspective view of a control unit housing and coupling of a display portion to the control unit housing.

FIG. 14 shows a simplified exploded view of internal components of the display portion 24. The front or top portion 128 of the exterior housing of display portion 24 is coupled to a back or bottom portion 130 by a series of fasteners 132 through a series of apertures 134. A pivot coupling assembly 194 includes a friction hinge 142 and a circular member 138 which includes a plurality of spaced apart apertures 140. A hollowed out semi-circular region of the display portion 24 includes a female end 180 and a male end 178. The pivotable coupling assembly 194 is position within the semi-circular region of the display portion 24 as shown by dashed lines 186, 188, and 190.

Corresponding female 184 and male 182 portions are provided in the upper end 26 of the exterior housing of the control unit 42. The pivot coupling assembly 194 thereby mates with the coupling portions 182, 184 as shown by dashed lines 186, 192. A suitable hinge 142 is the model MH40 manufactured by Reell Precision Manufacturing Corporation of St. Paul, Minn. (www.reell.com). The hinge 142 allows the display portion 24 to rotate between an upward or raised use position and a lowered or closed storage position as described above. However, the display may be stopped at any position in between the two extreme positions. The range of motion of the pivotable display portion is greater than 180 degrees.

The video display 24 includes a front or top housing 128, and a back or bottom housing 130. Within the two housing portions, which define an interior region, are provided a touchscreen 119 positioned above or on top of a liquid crystal display assembly 115. An insulator (not shown) is provided between the LCD assembly 115 and the printed circuit board or LCD board 121. An LCD cable 117 couples the display portion 24 to the algorithm control board 196 through an opening in the male portion 178.

Figure 15:
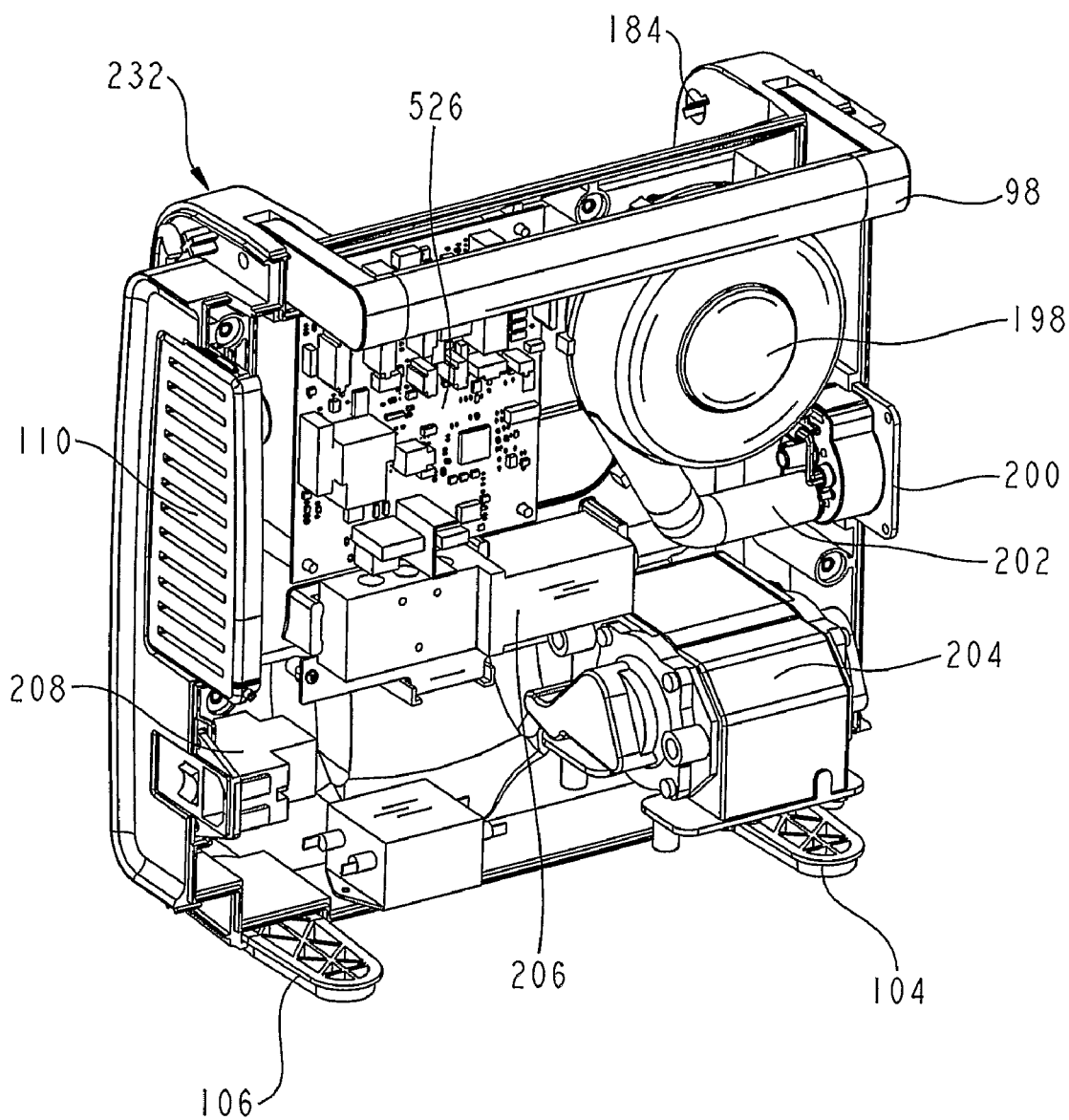
FIG. 15 is a perspective view of a control unit with a portion of the housing removed to show internal components.

FIG. 15 shows the control unit 42 with the rear housing 234 removed to show certain interior components of the control unit 42. The interior components of the control unit 42 include an algorithm control board 526, a blower 198, a hose connector 200, a hose tubing 202 coupling the hose connector 200 to the blower 198, a pump or compressor 204, a valve assembly 206, and a power input assembly 208. These components are described in greater detail below.

Figure 16:
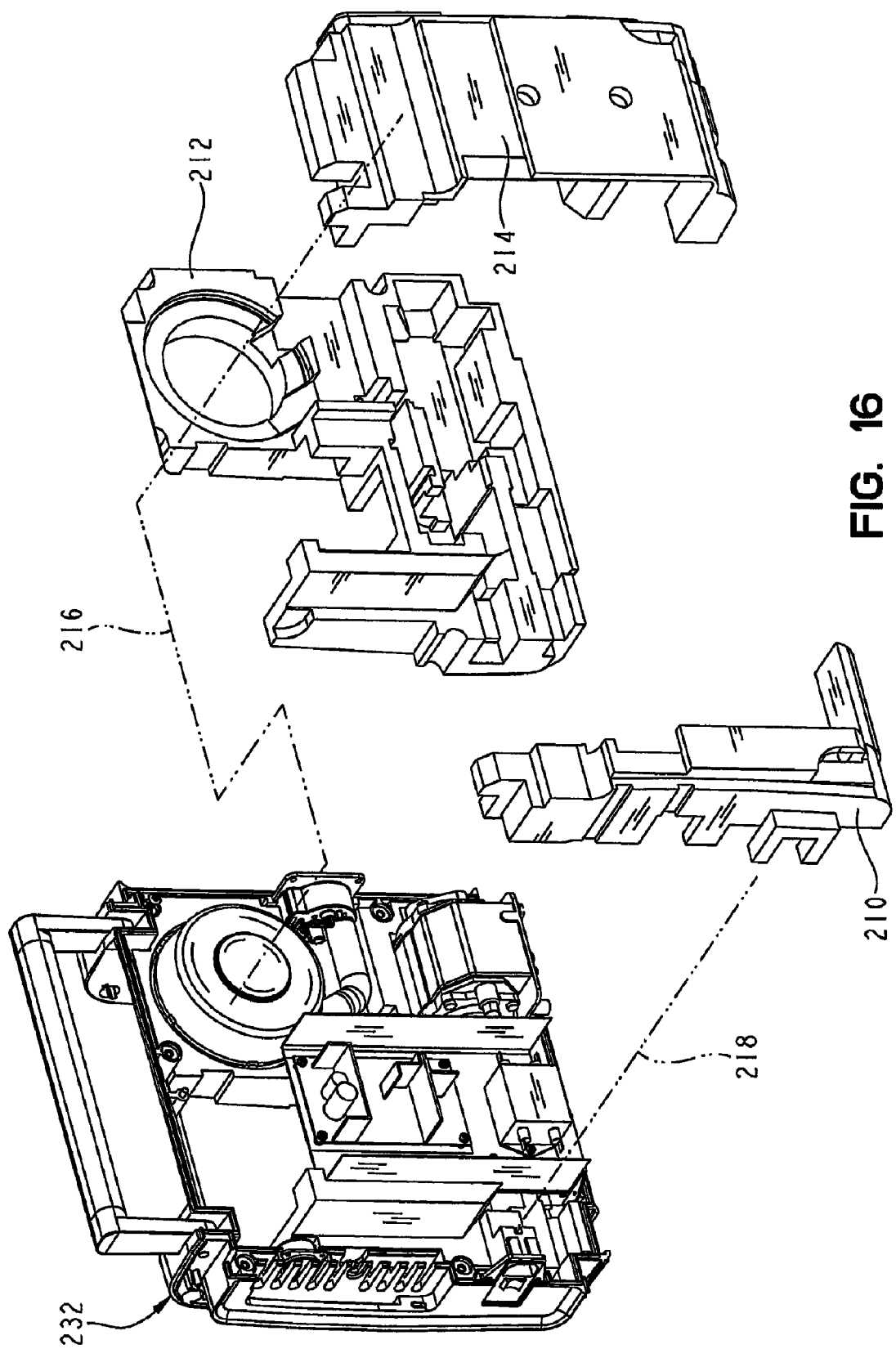
FIG. 16 is a perspective view of a control unit with a portion of the housing removed to show other internal components.

FIG. 16 illustrates a plurality of protective inserts 210, 212, 214 which are provided within the interior region of control unit 42. The inserts are aligned within the interior region of the control unit 42 as shown by dashed lines 216 and 218. Each of the inserts 210, 212, 214 is made of an insulating material such as EPAC (Electronic Packaging Assembly Concept) foam. The EPAC foam provides an internal chassis for the control unit 42. Each of the foam members 210, 212, 214 has within it one or more cooling channels which allow air to circulate. Such air channels (not shown) may also provide a channel for any leaking blower air to escape. The inserts 210, 212, 214 also function to dampen structural noise. In addition to the foam inserts 210, 212, 214, additional rubber mounting may also be provided, for example, on the compressor 204, in order to improve noise and/or vibration performance.

Figure 17:
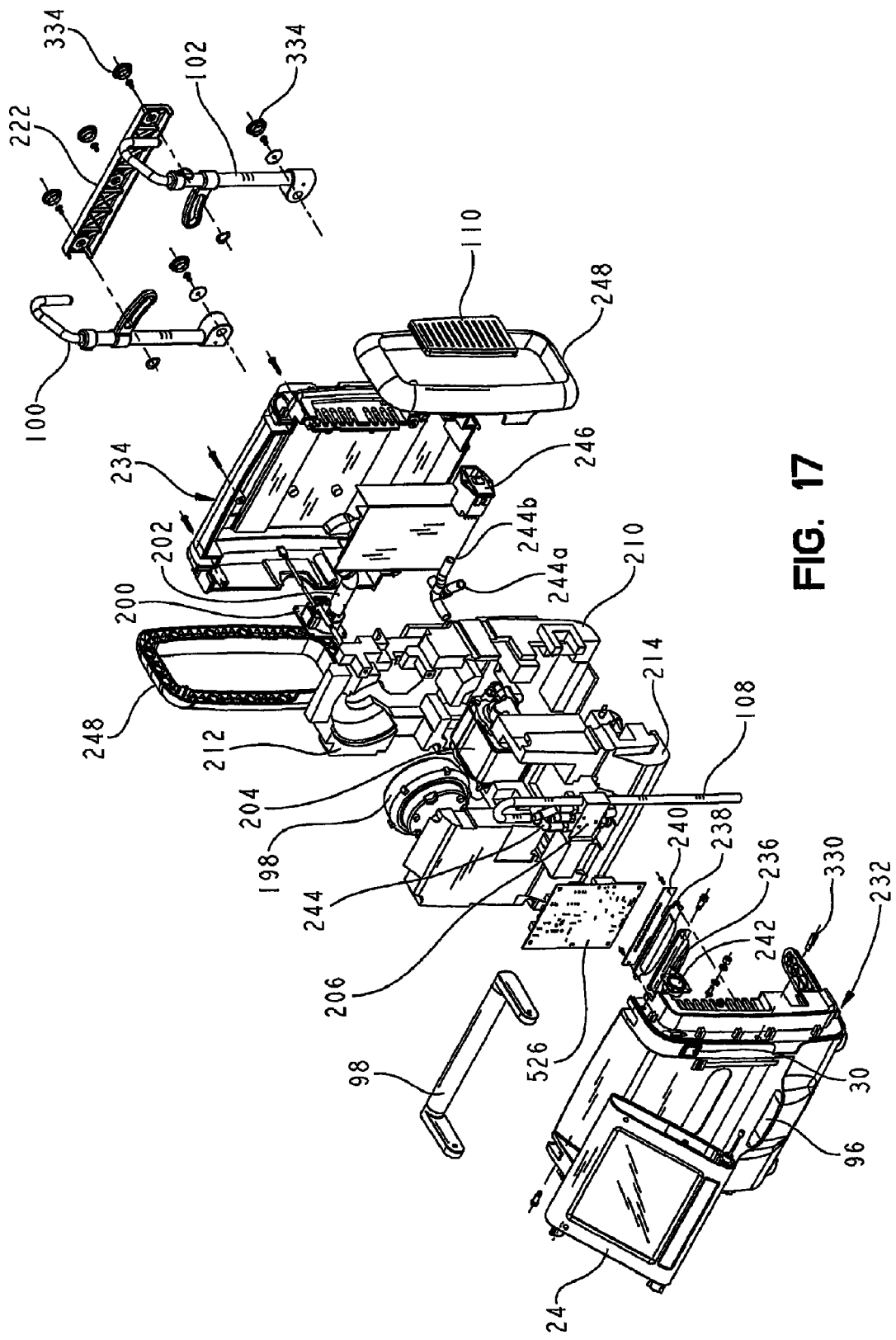
FIG. 17 is an exploded perspective view of internal components of a control unit from the perspective of a person facing the front side of the control unit.
Figure 18:
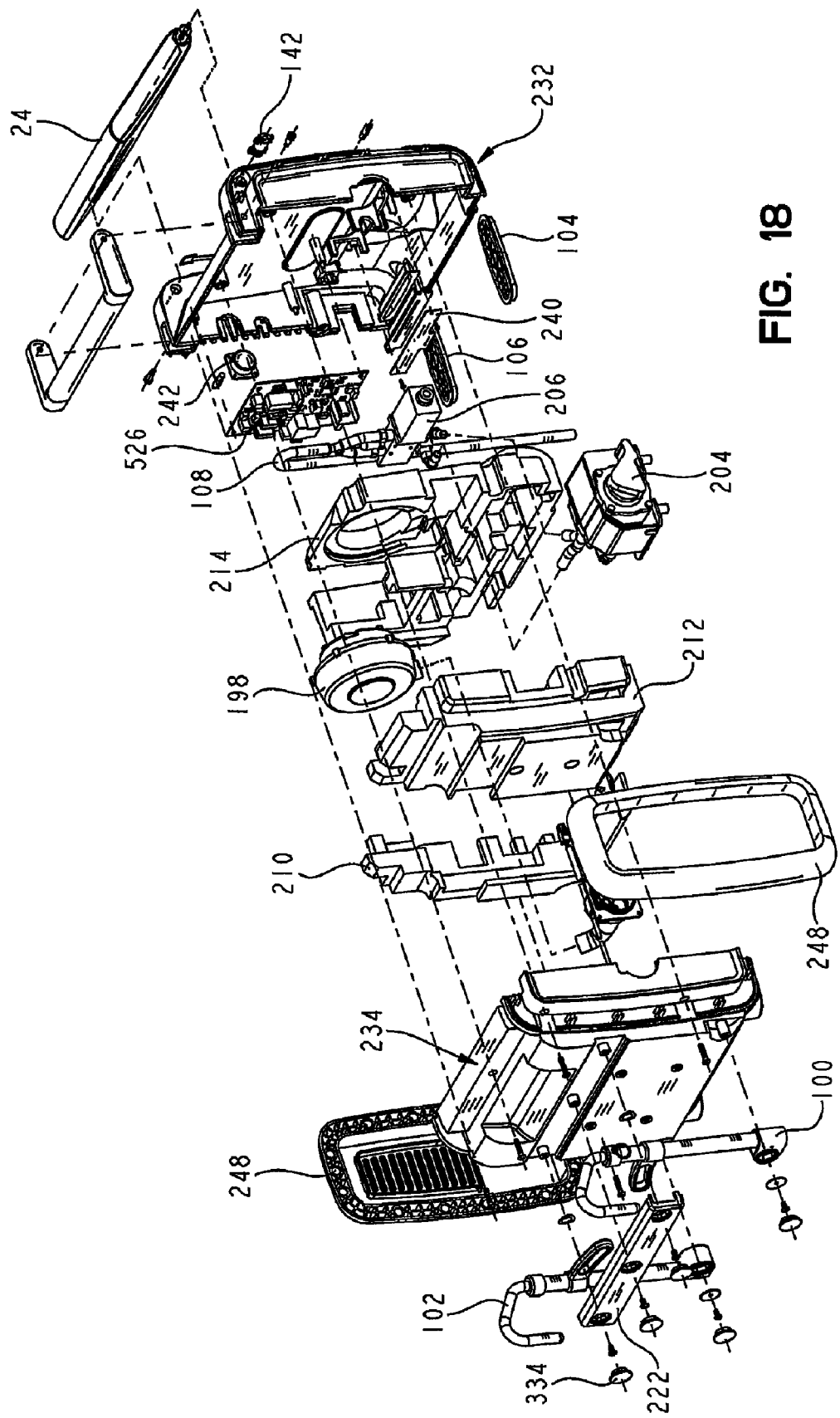
FIG. 18 is an exploded perspective view of internal components of a control unit from the perspective of a person facing the back side of the control unit.

FIGS. 17 and 18 show exploded views of interior components of the control unit 42. In FIG. 17, the components are viewed from the perspective of a person looking at the front housing 232. In FIG. 18, the components are viewed from the opposite perspective. Referring particularly to FIG. 17, front housing 232 includes the display portion 24, visual indicator or light bar 96, and CPR button 30. The handle 98 is pivotably coupled to the upper end 26 of the front housing 232.

The visual indicator or light bar 96 includes an LED lens 236, a lightpipe 238, and LED board 240. The LED lens 236 provides a clear surface for the LED light to penetrate. The lens may be textured or frosted to adjust the dispersion of light. The LED lightpipe 238 provides a path for the LED light to go through. The lightpipe 238 is made of a molded plastic. In the illustrated embodiment, the lightpipe 238 is divided into two parts for ease of moldability. The lightpipe 238 may be textured or frosted to adjust the dispersion of the light. The LED board 240 is coupled to the algorithm control board 196 to control the operation of the visual indicator or light bar 96.

The light bar 96 acts to visually alert a caregiver as to a situation involving the mattress 10, control unit 42, or patient, that may need attention. The light bar 96 may be illuminated in green, flashing green, or not illuminated at all, when the control unit and/or mattress is operating normally. The light bar may be illuminated intermittently to indicate different modes of normal operation. For example, steady green may indicate pressure relief mode while flashing green may indicate another mode (such as maxinflate, turn assist, etc.) A different mode (such as steady on flashing yellow or amber) may be used to indicate when either the control unit or the mattress is in need of service or when an alarm (such as a bed exit alarm, described elsewhere herein) is activated. Yet another mode (such as steady or flashing red) may be used to indicate that the CPR function of the mattress is turned on, that the patient appears to be showing signs of inactivity or distress, or for other purposes. For example, the light bar 96 may be coupled to the motion monitor feature discussed elsewhere herein so that another visual alert is generated (an orange light, for example) if the patient's motion is above or below an acceptable range. Also, the light bar 96 may be coupled to one or more of the bed alarm settings discussed elsewhere herein so that a visual alert is generated if the patient is attempting to exit the bed, or lying near the edge of the bed, for example.

The front housing 232 supports the foam insert 214, into which most of the interior components are loaded. The front housing 232 outlines and supports the LED lens 236, light type 238, and holds the speaker 242 on its flange. The front housing 232 is made from Noryl structural foam sufficient to withstand applicable drop test requirements.

The handle 98 is attached to the front housing 232 by a pair of shoulder screws. The handle is blow molded in polycarbonate. The algorithm control board 526 is described elsewhere herein, for example with reference to FIGS. 7 and 19.

The air line 108 is coupled to the switching valve 206 by the inlet and outlet tubing 244. Separate tubing 244a, 244b is provided for inlet and outlet hoses.

The blower 198 is a commercially available blower such as Ametek model no. 150166-00. The compressor 204 is a commercially available compressor such as Thomas model no. 6025SE-XP, part no. 950115. The switching valve 206 is a pressure/vacuum valve such as is commercially available from Numatics model no. 92114-2. The various pneumatic tubing used to interconnect the pneumatic items in the control systems are generally conventional pneumatic tubing. Also, various connectors and wiring are used to interconnect the electrical items in the control unit 42 and the patient support 10. Rubber bumpers and screw caps are used to cover and hide screws and other fasteners on the control unit assembly. A plurality of labels or label portions 332 (FIG. 12) are provided as needed to meet marketing and regulatory requirements.

The power input 246 includes a power supply, for example XP model no. ECM130PS12, a power inlet, for example Corcom model no. PE0S0DBX0, and a 120V power filter, such as Corcom model no. 3MZ1.

The foam inserts 210, 212 hold other components in place, for example the insert 212 keeps the blower, compressor, and power supply in position, and the insert 210 keeps the power supply, speaker, and power inlet in proper position. The insert 214 is also made of EPAC (Electronic Packaging Assembly Concept) foam and is used to hold the algorithm control unit, compressor, blower, switching valve, and power supply in place. The use of these foam inserts 210, 212, 214 eliminates the need for a metal chassis and fasteners.

The first and second end caps 248 conceal the screws and other molding issues on the front and back housing 232, 234. The end caps are made from Santoprene Thermo Plastic Rubber (TPR). The end cap 248 also provide cushioning for protection during impacts and drops. The first end cap 248, positioned proximate to the friction hinge 142, also includes a set of ribs to help keep the friction hinge in place. It should be noted that the housing portions 232, 234, 248 are interlocking walls designed to prevent liquid ingress.

The filter holder 110 positions the foam air filter and maintains it in front of the air inlet ports on the front and back housing 232, 234. The filter 110 is molded in polycarbonate.

The hose receptacle 200 receives and holds the hose end. The receptacle 200 also holds a gasket to prevent air leakage. Attached to the receptacle are one or more air lines and electrical contacts (i.e., three and eight, respectively, in the illustrated embodiment). The receptacle to 100 is made from Valox or another very strong material. The receptacle 200 is held in place by the front and back housings 232, 234. The receptacle and corresponding hose are described in greater detail in U.S. Provisional Patent Application Ser. No. 60/636, 252, assigned to the assignee of the present invention, and incorporated herein by reference.

The hose itself includes the electrical contacts and air lines that connect directly to the patient support 10.

The rear housing portion 234 holds and compresses the back and side foam insert 212, in order to hold all of the internal components in proper position. The rear housing 234 also provides mounting points for the hanger assembly 100, 102 and holds the speaker 242 in place. Rear housing 234 is made from Noryl structural foam sufficient to withstand applicable drop test requirements.

The control unit 42 may be attached to a footboard or other portion of a bed frame, or may be positioned on the floor. Hook assemblies 100, 102 are provided in order to attach the control unit 42 to a portion of a bed, i.e., a footboard. The hooks are configured to support at least four times the weight of the control unit 42, without failing. Each of the hooks 100, 102 may be rotated or otherwise reconfigured in various positions in order to adapt to a variety of different footboards or other bed portions. A similar suitable hook assembly is described in U.S. Pat. No. 6,735,799 to Ellis, et al., assigned to the assignee of the present intervention and incorporated herein by this reference.

Feet 104, 106 are provided primarily to stabilize and protect the control unit 42 when it is positioned on the floor. The feet 104, 106 are made of rubber in the illustrated embodiment.

A pivot cover 222 is provided to hold the top pivots of the hook assemblies 100, 102 coupled to the rear housing 234. The cover 222 also is adjustable to control the clearance between the cover 222 and the hooks 100, 102.

A rubber detent 330 is provided in order to hold the display portion 24 in place, i.e., in the storage or downward position, for example during transport of the control unit 42. These detents 330 provide a resistance to upward rotation of the display portion 24.

Figure 19:
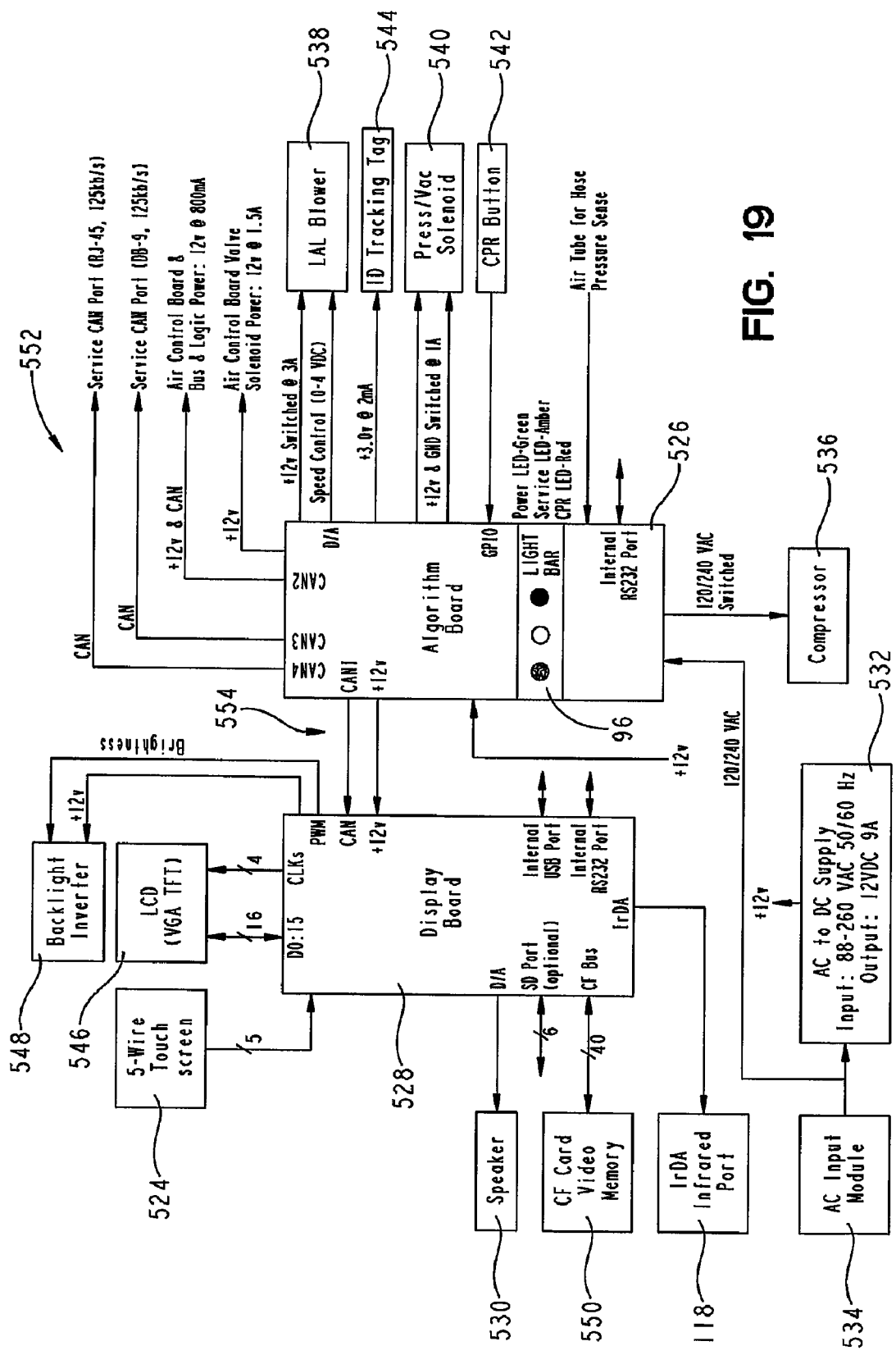
FIG. 19 is a schematic block diagram of an internal architecture of a control unit.

As noted above, the control unit 42 provides the user interface, mattress interface, mechanical system, and control for the mattress 10. FIG. 19 is a simplified system level block diagram for the control unit 42. FIG. 19 shows the major components of the control unit 42, including the display board 528 and the algorithm board 526. In the illustrated embodiment, the display board 528 and algorithm board 526 provide the control functions for the entire mattress system.

The display board 528 provides the primary interface between the end user, technician, or caregiver and the mattress system. The display board 528 also contains the mattress system's user interface.

In the illustrated embodiment, the user interface includes a touchscreen video display. The display board 528 is also capable of playing video files stored in a memory 550, using commercially available software such as Windows Media Player. Such video files may be used, for example during system installation and user training. The display board 528 is also responsible for storing user data and providing access to that data via its IRda infrared port 118. The display board interfaces to the algorithm board 526 and to the rest of the mattress system via a CAN bus connection 552, 554.

The algorithm control board 526 controls the normal working of the mattress system by executing algorithms that convert user requests into desire actions. These algorithms may be executed, for example, to set proper mattress pressure distribution for a patient, detect patient position, and/or provide patient turning assistance using the turn assist bladders 74.

As noted above the algorithm board 526 provides a CAN bus connection 552 for other system components. The algorithm control board 526 also provide speed control for the blower 198, which is used primarily for mattress service cooling. The algorithm control board 526 also provides power for an ID tracking tag 544 and control of a pressure/vacuum switching valve 540, which allows for inflation and quick deflation of one or more portions of the mattress 10. The algorithm control board 526 also provides switched AC power to the system's compressor 204 via an optically isolated triac circuit. The CPR button 542 is also connected to the algorithm board 526.

Electrically coupled to the display board 528 are the infrared port 118, the memory 550, the speaker 530, the touchscreen 524, the liquid crystal display 546, and the backlight inverter 548.

Figure 20:
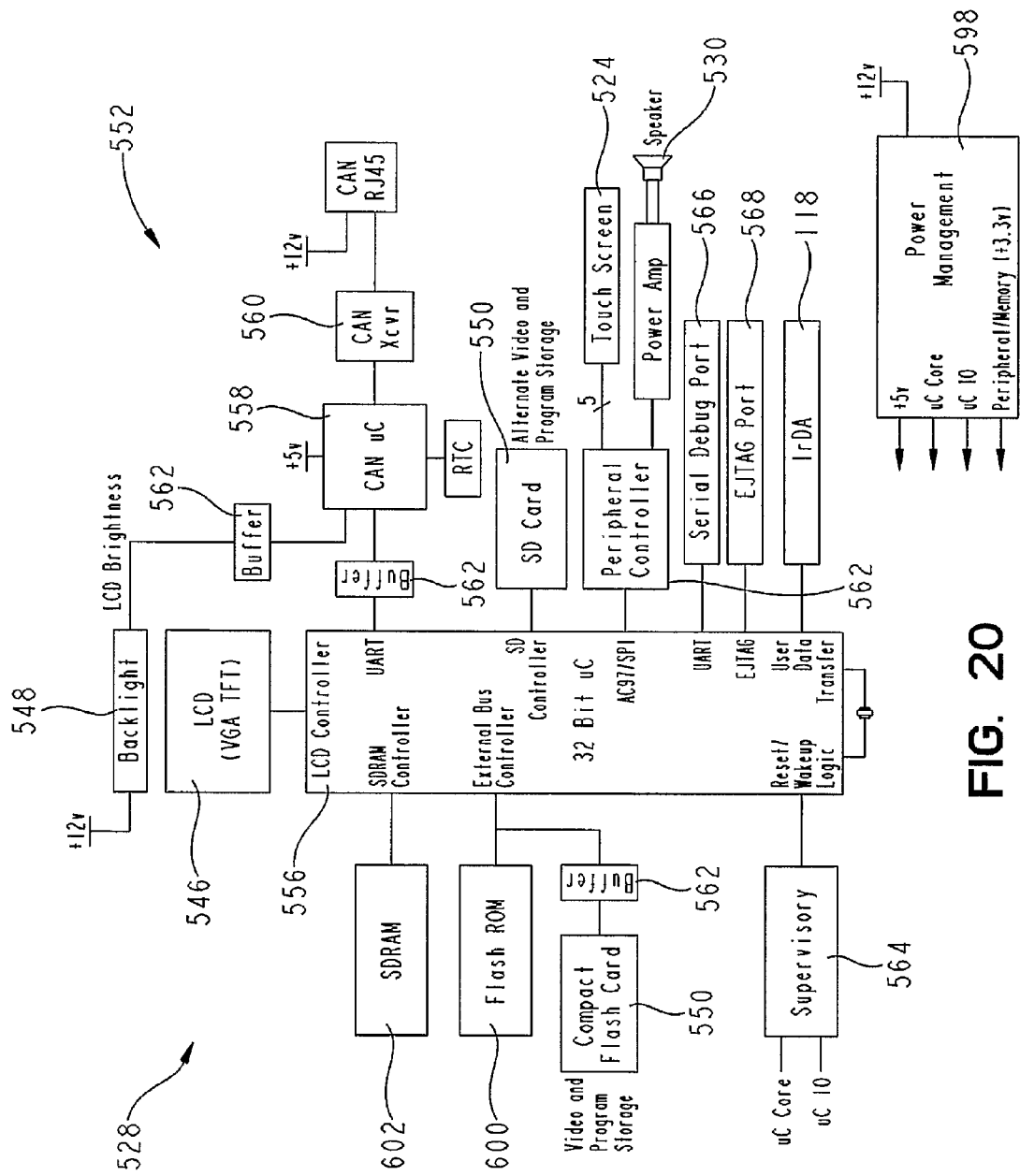
FIG. 20 is a schematic block diagram of an internal architecture of a display board of a control unit.

The display board architecture is shown in more detail in FIG. 20. FIG. 20 is a simplified block diagram for display board 528. The display board 528 includes a 32 bit microcontroller 556. In the illustrated embodiment an AMD Au1100 32 bit microcontroller is used. Other suitable microprocessors include the Intel Xscale and Freescale IDOTMX21. A CAN microcontroller is coupled to the main microcontroller 556 in order to provide the CAN function. In the illustrated embodiment the CAN microcontroller 558 is an Atmel T89C51CC01. Coupled to the CAN microcontroller 558 is a CAN transceiver 560. In the illustrated embodiment, the transceiver is a Philips TJA1054. The CAN controller 558 communicates with the main microcontroller 556 through a UART. A level shifting buffer function 562 is provided between these two devices. Optionally, the CAN controller 558 may also be used to vary the video display's backlight brightness using one of its pulse width modulated outputs. The CAN controller 558 also provides a serial interface to the real time clock of the display board 528.

As shown, a compact flash card or other suitable memory 550 may be coupled to the display board microcontroller 556. In this way, training videos or other types of videos, for either or both a caregiver and technicians installing using or setting up a patient support 10 may be stored on removable flash memory cards which may be connected to the microcontroller. The flash memory cards 550 may also provide a means for updating software applications and the system operating system. A suitable flash memory card is the Secure Digital (SD) card, however, the Compact Flash (CF) card also has the required capabilities and would work equally as well. The display board 528 as shown will support either a CF card or a SD card.

The primary function of the CAN microcontroller 558 of the display board 528 is to translate CAN messages from the mattress system into RS232-based messages for one of the display microcontroller 556, and to format the display microcontroller's 556 serial messages into CAN messages and send them out on the CAN bus. The CAN microcontroller 558 has a 80C51COR, 32 kilobytes of flash memory, 2 kilobytes of flash memory for a bootloader, 2 kilobytes EEPROM storage for variables, and a full duplex UART. The real time clock is implemented by a Dallas semi-conductor DS13O7Z, which is connected to the serial bus of the CAN microcontroller 558. Power is provided to the real time clock by its own independent battery. The LCD backlight 548 is implemented using a PWM output of the CAN microcontroller 558. The reset of the display microcontroller 556 is implemented by buffering an output of the CAN microcontroller 558 to a reset pin of a supply voltage supervisor 564.

Development of a CAN microcontroller 558 may be accomplished using standard C programming and microcontroller emulation tools, as well as several commercially available CAN tools such as Micro Vision, Keil 8051 software tools for C, and CANalyzer ProCAN. The CAN microcontroller 558 acts as the protocol interface between the display board microcontroller 556 and the rest of the mattress system. The CAN microcontroller 558 provides firmware of great capabilities and also performs self test each time it is powered. The CAN microcontroller 558 is a pure-2-peer bus, therefore, all messages communicated are available to each component on the bus. Each individual component, therefore, determines which CAN messages require its attention.

The touchscreen user interface 524 is a 5-wire overlay that is controlled by a peripheral controller. The peripheral controller 562 controls the touchscreen and also provides a digital to analog converter for the audio output to a power amplifier that drives the speaker 530. The peripheral controller is any controller that has both an audio driver and a 5-wire touchscreen controller such as a Wolfson WM9712L.

A serial debug port 566 is provided for software debugging and also for possible field upgrades, for example by a technician. A serial debug port 566 connects to a second UART port of the display microcontroller 556.

An EJTAG port 568 is provided. The display microcontroller 556 utilizes the EJTAG port 568 for program monitoring, debugging, and access to the MIPSCORE.

The IRda port 118 provides electrically isolated data transfer for the display board 528. The infrared port 118 is built into the display microcontroller 556 and supported in software.

The power of management circuitry 598 provides power-up and reset circuitry for the display board 528. This circuitry is designed to correctly bring the display micro 556 out of a cold power up or out of a warm reset. The power of management circuitry 598 also regulates power for the peripheral devices CAN, memory, peripheral controller.

The display board 528 also include memory. The illustrated display board 528 supports either or both 128 mega bits SDRAM and 64 mega bit flash memory. The liquid crystal display 546 is, in the illustrated embodiment, a TFT VGA LCD (640×480) with a TTFL backlight.

Figure 21:
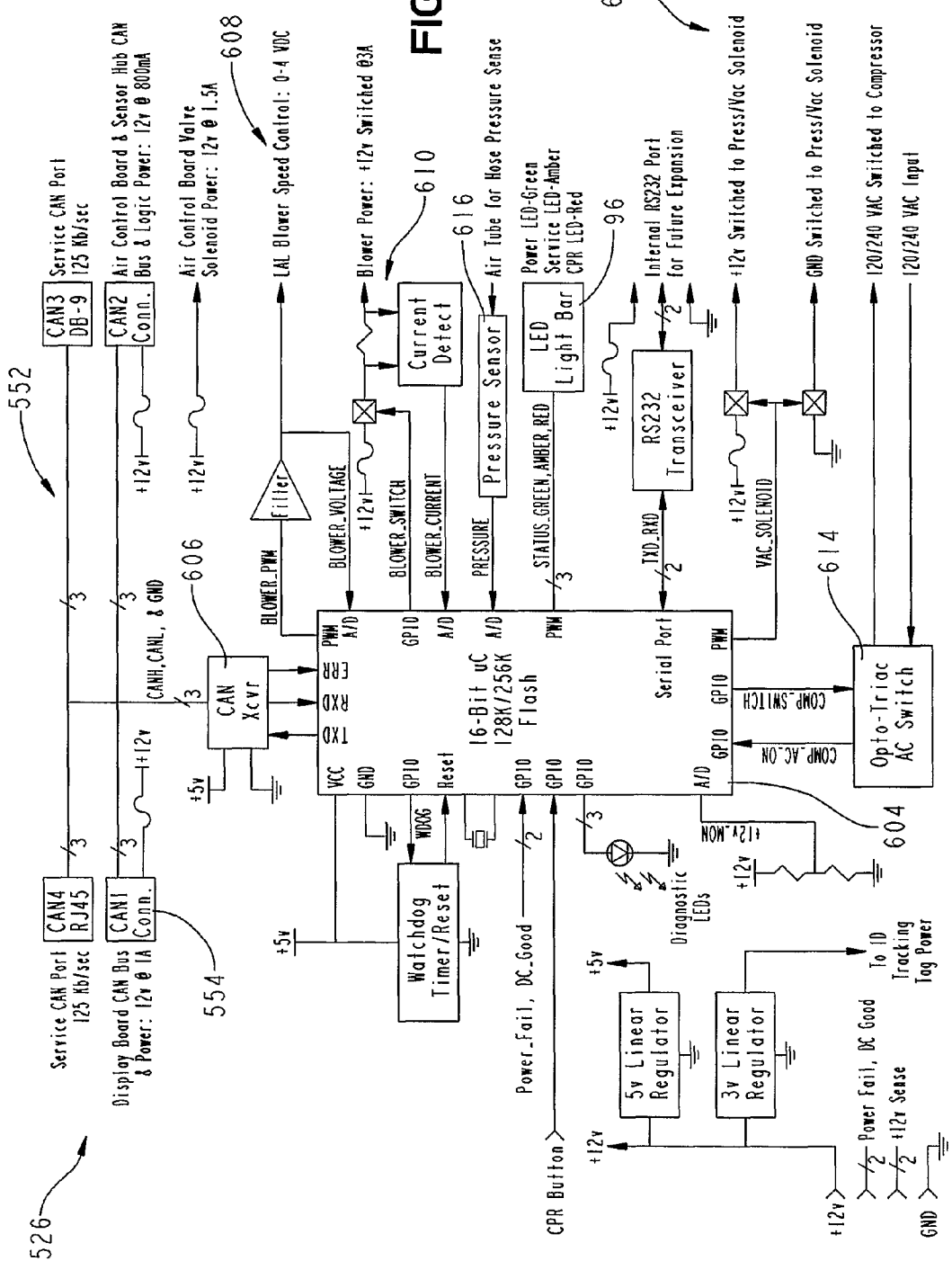
FIG. 21 is a schematic block diagram of an internal architecture of an algorithm control board of a control unit.

A simplified block diagram for the algorithm board 526 is shown in FIG. 21. The algorithm board 526 receives converted user directives received by the display board 528 and sent over to CAN bus 554. The algorithm board 526 than takes the appropriate action by interacting with the remaining system components. In addition, the algorithm board 526 directly controls the CPR button 542 and also a diagnostic LED light bar 96, which may be used for trouble shooting on other purposes.

The microcontroller 604 for the algorithm board 526 is the Motorola Free Style MC9S12DJ128BCFU or other suitable 16-bit microcontroller with a 128 kilo bit flash EEPROM that can be upgraded to 256 kilo bits if necessary. The algorithm control microcontroller 604 includes 8 kilo bits of RAM memory, 2 UART ports, and 7 eight-bit PWM channels also, the algorithm control micro 604 has a built in CAN controller, which supports the current versions of CAN.

The software for the algorithm board 526 was developed using commercially available development tools such as Code Warrier, Metro Werks Professional Edition C compiler. The algorithm control board microcontroller 604 may also be a Renesas (Mitsubishi) M306N5FCTFP or Renesas, (Hitachi) HD64F2623. The algorithm control board microcontroller 604 may be any other suitable microcontroller having the required architecture, onchip in-application programming with flash memory, ability to expand the memory without changing the host board, CAN channel, CAN drivers, and required drivers support.

The CAN bus connection 552 includes RJ-45 connectors for all system resources that require access to the CAN bus. A Phillips TJA1054 CAN transceiver or other suitable CAN transceiver 606 is used to interface the microcontroller 604 to the CAN bus 552, 554.

Power is supplied by the mattress system to the algorithm board 526. The algorithm board linearly regulates the power supply for the board's own logic supply. The system's power supply is also linearly regulated for the ID tracking tag 544. The algorithm 526 also distribute power to the display board 526 sensor hub 508 and air control board 512.

As mentioned above, the blower 198 provides high volume low pressure air circulating through a portion of the patient support 10. The microcontroller 604 controls the speed of the blower 198 through a PWM output 608. The algorithm control microcontroller 604 also provides power to the blower motor via a high current connection 610, which is monitored by one of the microcontroller's A/D input. The microcontroller 604 can disable the blower's power if an abnormal current is sensed.

The microcontroller 604 also controls and activates or deactivates the pressure/vacuum valve solenoid 206, which is located within the control unit 42. The microcontroller output 612 are used to control a solenoid driver which activates the switching valve 206. One GPIO pin is provide on the ground side of this solenoid and another GPIO pin is provided on the high side of this solenoid. This high and low side control provides the ability to turn off the solenoid, even if a single component failure occurs in the driver circuit. PWM control of the high side switch also provides the ability to duty-cycle and reduce the average solenoid current, 'once the solenoid has pulled in'.

Another output of the microcontroller 604 is used to control an optically isolated triac switch 614 for the application of switched AC power to the compressor 204. The triac circuit 614 also detects when switched AC is present and optically couples this information back to a microcontroller input for monitoring purposes. A pressure sensor input 616 is also connected to the microcontroller 604 as described above.

Referring back to FIG. 19, the touch screen 524 includes a resistive 5-wire touchscreen which is used in connection with a liquid crystal display 546. While less expensive 4-wire touchscreens may also be used, the 5-wire touchscreen is presently preferred. A suitable touchscreen is the Elo Accutouch® 8.4 inch touch screen part no. E24724-000. An Elo and Intellitouch surface way touchscreen may also be used.

As described above, the touchscreen 524 is used to display mattress control information and options to a caregiver, technician, or other end user, and receive as input directives from the end user. The remaining figures show examples of user interface screens implemented using touchscreen 524.

FIGS. 22A and 22B illustrate user interface screens for a patient support that does not have a patient positioned upon it. In FIGS. 22A and 22B, a graphical depiction of the patient support 622 indicates that at the present moment, the head section of the patient support 10 is raised. The user interface includes a first display portion 618 and a second display portion 620. The graphical depiction of the patient support 622 is provided within the second display portion 620. The first display portion 618 includes a plurality of buttons 624, 626, 628, 630, 632. Each of these buttons, in the illustrated embodiment, is activatable by human touch or contact with another object. When one of these buttons is activated, an aspect of the button's presentation or molding changes. For example, in FIG. 22A, a keylock button 626 is darkened to show that the keylock button 626 is activated. When the keylock button 626 is activated none of the other buttons are available. The buttons are indicated as not being available by a change in an aspect of the button's presentation, such as by being grayed out as shown. If the keylock button 626 is activated, then contact with any of the other buttons 624, 628, 630, 632 will not result in the associated function being performed. Contact with the keylock button 626 when it is in the activated mode operates to deactivate the keylock and unlock the touchscreen. The touchscreen 524 will then remain unlocked for a period of time, for example 2 minutes, or until the keylock button 626, or another button, is activated. When the touchscreen 524 is unlocked, the keylock button 626 appears grayed out and the other available function buttons appear darkened. FIG. 22B shows the touchscreen 524 with the keylock 626 turned off.

The menu button 624, if activated, brings up a plurality of additional menu options for controlling different features of the patient support 10. The left and right turn assist buttons 628, 630 control the turn assist bladders 74A and 74B. Activation of the left turn assist button 628 results in the left turn assist bladder being inflated to assist the caregiver in rotating a patient positioned on the mattress 10. Activation of the right turn assist button 630 similarly activates the right turn assist bladder to rotate the patient in that direction. Activation of the maxinflate button 632 results in the patient support 10 being over inflated, for example, for CPR therapy.

FIGS. 22C and 22D show similar touchscreen displays with the graphical depiction 622 of the patient support 10 shown in the horizontal position, indicating that the mattress 10 or any portion thereof, is not elevated.

Figure 23:
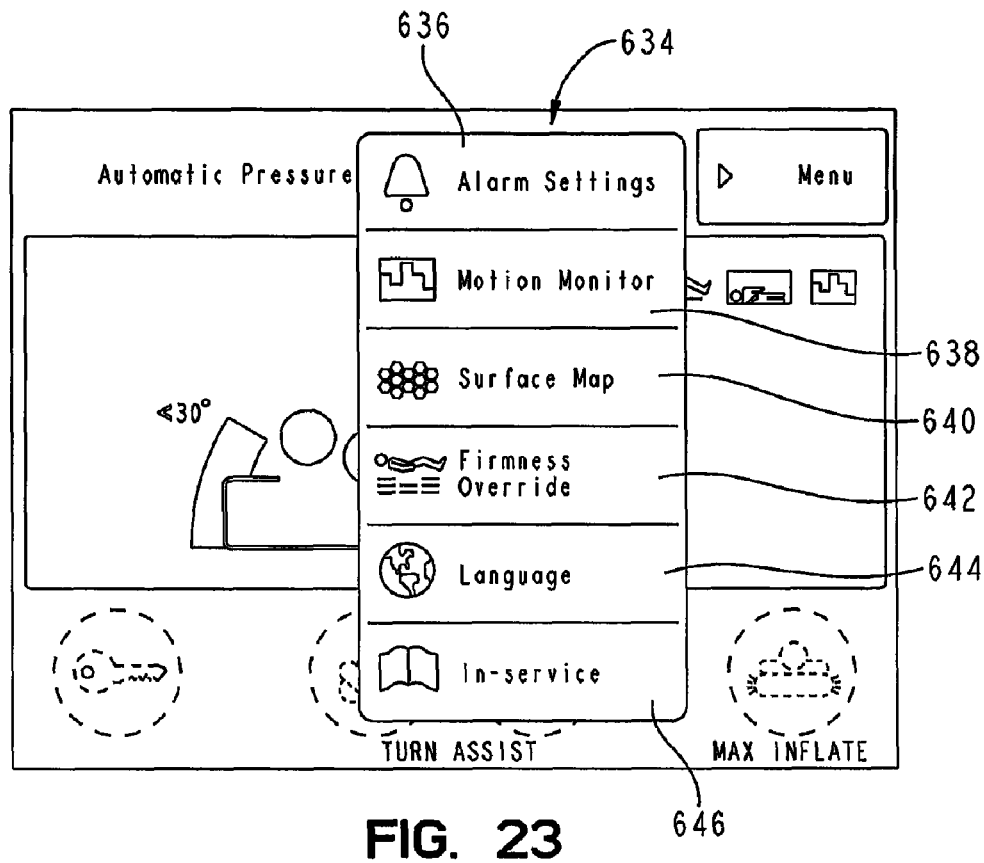
FIG. 23 is an exemplary user interface for a pull down menu for a control unit.

FIG. 23 shows a pull down menu that becomes active when the menu button 624 is depressed. The pull down menu includes a plurality of menu options including alarm settings 636, motion monitor 638, surface map 640, firmness override or "comfort adjust" 642, language 644, and in service 646. Each of these menu options will be described below.

Figure 24:
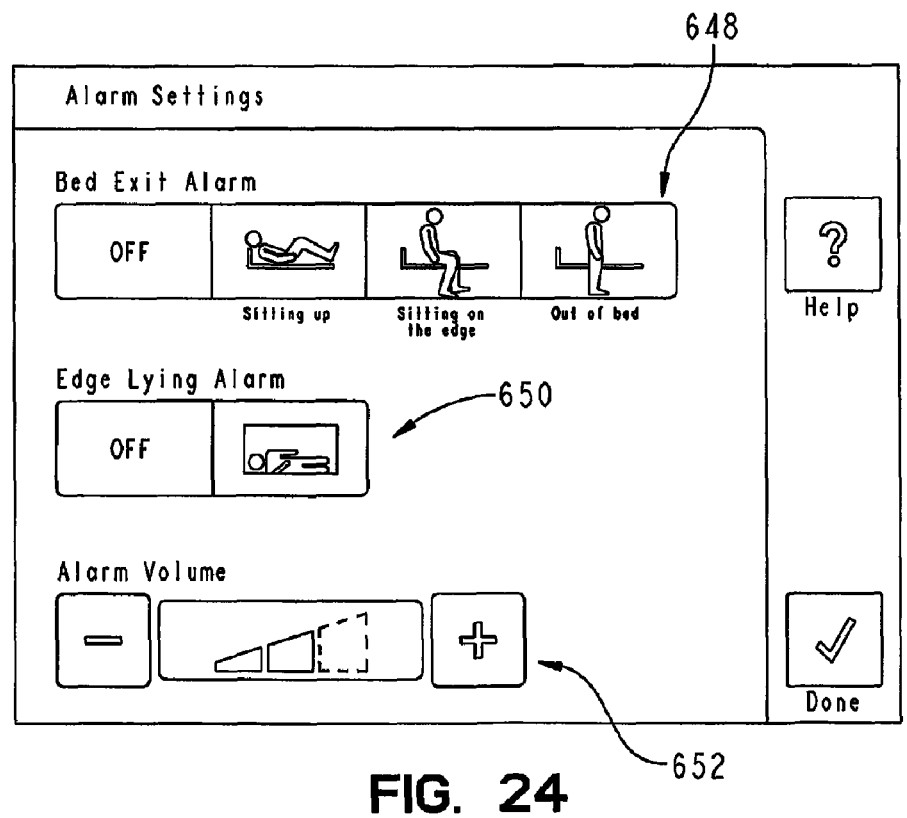
FIG. 24 is an exemplary user interface for configuring alarm settings of a control unit.

When the alarm settings button 636 is activated, a screen such as is shown in FIG. 24 is then displayed. The alarm settings portion of the user interface is used for a caregiver or other enduser to configure various available alarms, which would alert a caregiver when the patient may be moving into a position of danger. For example, a bed exit alarm 648 is provided whereby the caregiver may configure the control unit 42 to alert the caregiver when the patient appears to be preparing to exit the bed. As shown in FIG. 24, there are a number of possible types of bed exit alarms, including sitting up, sitting on the edge, and out of bed. Thus, the caregiver can elect to be notified when the patient is sitting up, when the patient appears to be sitting on the edge of the bed, or when the patient is already out of the bed. The buttons are activated by contact, and when a button is activated, its presentation is changed as shown.

Another available alarm option is the edge-lying alarm 650. If the edge-lying alarm 650 is active, a caregiver will be notified when the patient is laying up against the edge of the bed.

Once the caregiver has elected the desired alarm type, the caregiver can then alter the alarm volume by pressing the plus or minus button 652. A graphical display of molded bars indicates the relative loudness of the alarm. As described herein, the alarm is an audible signal, however, it could also be a visual or electronic signal or other appropriate type of alert. A similar adjustment for display screen brightness control may also be included.

Figure 25A:
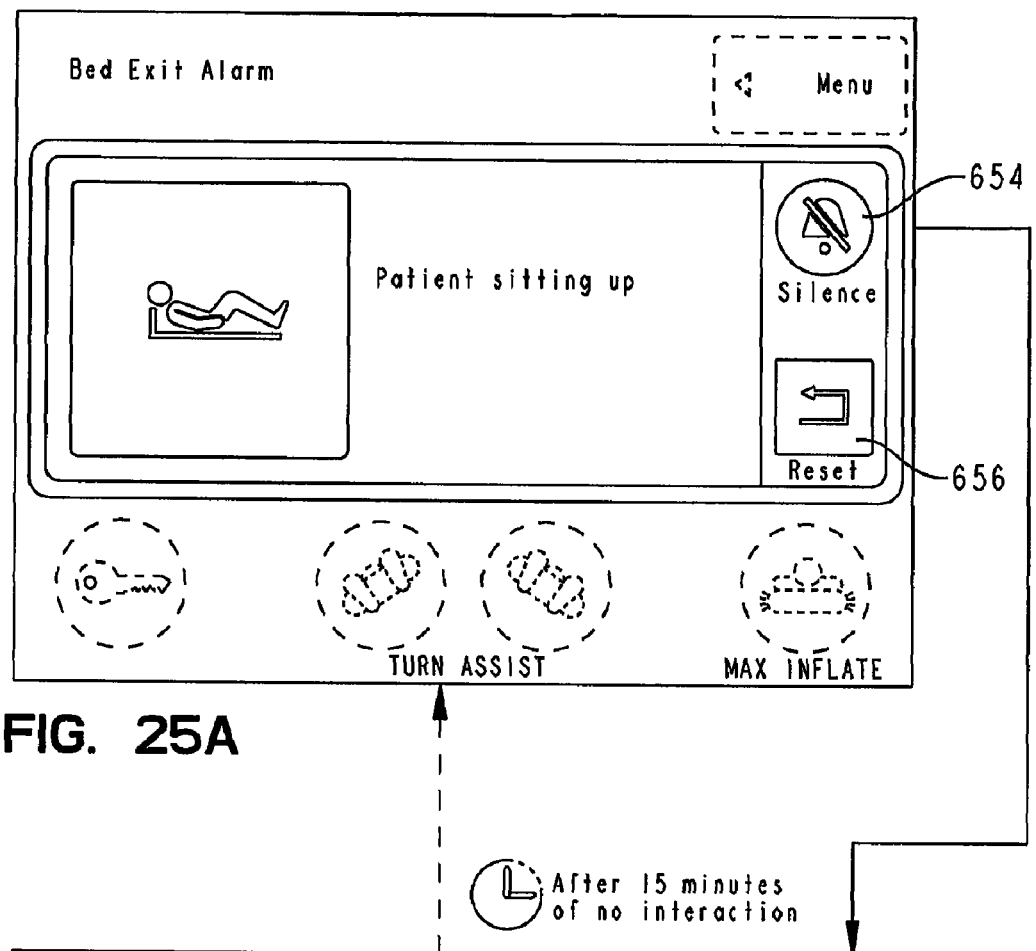
FIGS. 25 A-D are exemplary user interfaces for configuring selected alarm types.
Figure 25B:
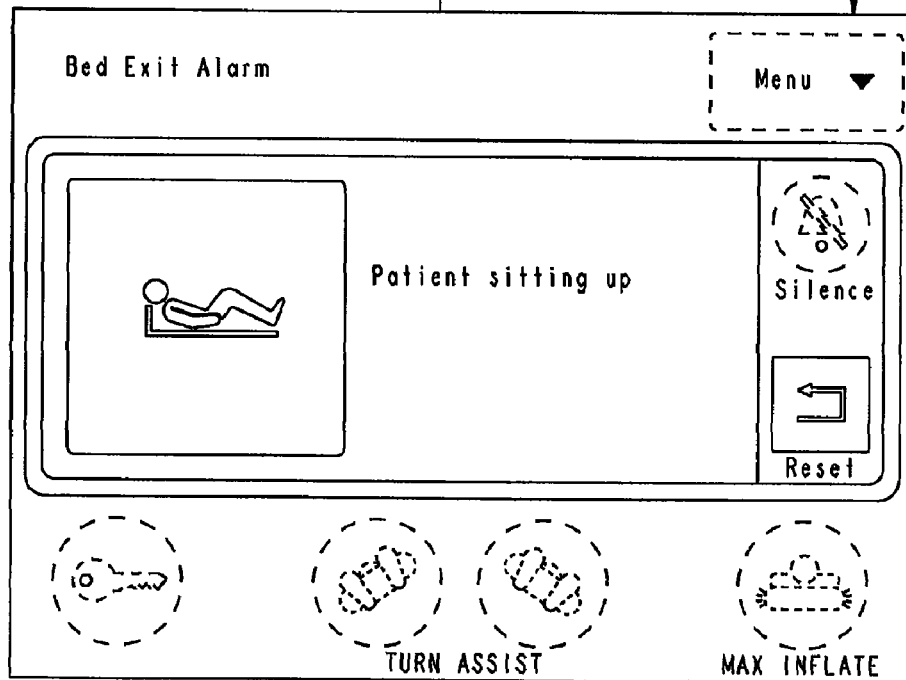
Figure 25C:
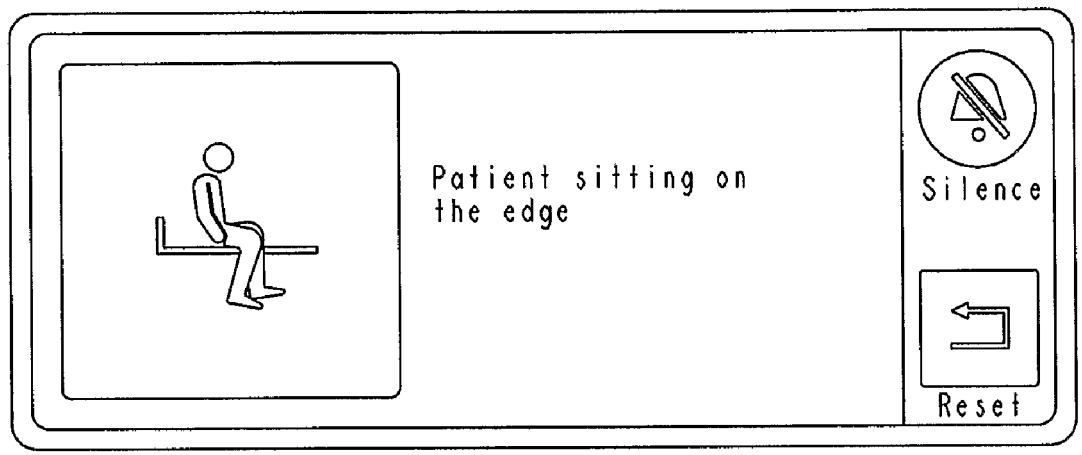
Figure 25D:
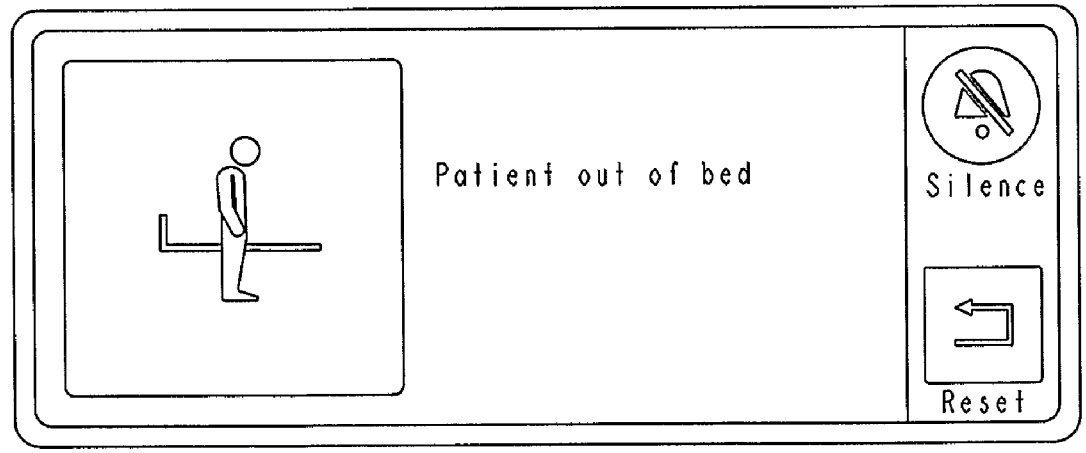

FIGS. 25A-D show examples of pop up user interface windows that may be presented in response to selection of a corresponding bed exit alarm. These pop up windows correspond to the selected button 648 shown on FIG. 24. For example, when the sitting up button 648 is activated, the sitting up window shown in FIGS. 25A and 25C is presented to the end user. The pop up window includes a silence button 654 and a reset button 656. The silence button 654 is used to deactivate the alarm. The reset button 656 is used to reconfigure the alarm, or reset the alarm parameters to its previous settings. The pop up window shown in FIG. 25A is displayed with the button 654, 656 darkened in as activated for a period of time, for example fifteen minutes, unless one of the buttons is activated. If no button is activated after the period of time expires, then the buttons are deactivated as shown in FIG. 25B. FIGS. 25C and D illustrate similar pop up windows for other available bed exit alarm selections. FIG. 25C illustrates a pop up window for the patient sitting on the edge of the bed alarm, and FIG. 25D illustrates a pop up window for the patient out of bed alarm. Note that the graphical depiction of the patient shown in the left hand portion of the pop up window changes depending upon the alarm type selected. If the sitting up bed exit alarm is selected, an alarm will sound when the patient moves away from the head section of the mattress. Thus, the sitting up alarm is a more sensitive alarm as it typically alerts a caregiver when the patient first begins to move.

When the sitting on the edge of the bed alarm is selected, an alarm will sound when the patient moves away from the center of the mattress toward an egress point. This setting typically alerts a caregiver when the patient is preparing to exit the bed. The out of bed alarm will sound when the patient's presence is no longer detected by the mattress 10. If the out of bed alarm is selected, the patient is able to move freely within the bed without triggering an alarm, but the caregiver is alerted if the patient leaves the bed.

FIGS. 26A-26B show similar user interface pop up windows that are displayed if the edge-lying alarm 650 is activated. When the edge-lying alarm is selected, an alarm will sound when the patient is lying off center, on either edge of the bed. When this setting is used, the caregiver is alerted if the patient may be lying against the side rails or appears to be in danger of rolling out of the bed.

The pop up windows shown in FIGS. 25C-25D illustrate a portion of the motion monitoring feature 638. In general, the motion monitoring feature enables caregivers to monitor the level of activity of a patient on the mattress 10 over a period of time. For example, in FIG. 26C, a pop up window indicates that the patient's level of activity has been below a threshold motion monitoring level for a period of ninety minutes. As configured, the caregiver was not alerted as to a change in the patient's level of activity. The time period for triggering an alert may be customized. The motion monitoring features are described in greater detail in U.S. patent application Ser. No. 11/119,635, filed May 2, 2005, assigned to the assignee of the present invention and incorporated herein by reference.

In the illustrated embodiment, the alarm settings and motion monitor portions of the user interface include graphical depictions illustrating the particular feature, i.e., a person lying next to the edge of the bed in the case of the edge lying alarm. The graphical depiction changes depending on the particular alarm setting or motion monitor feature selected.

Figure 27:
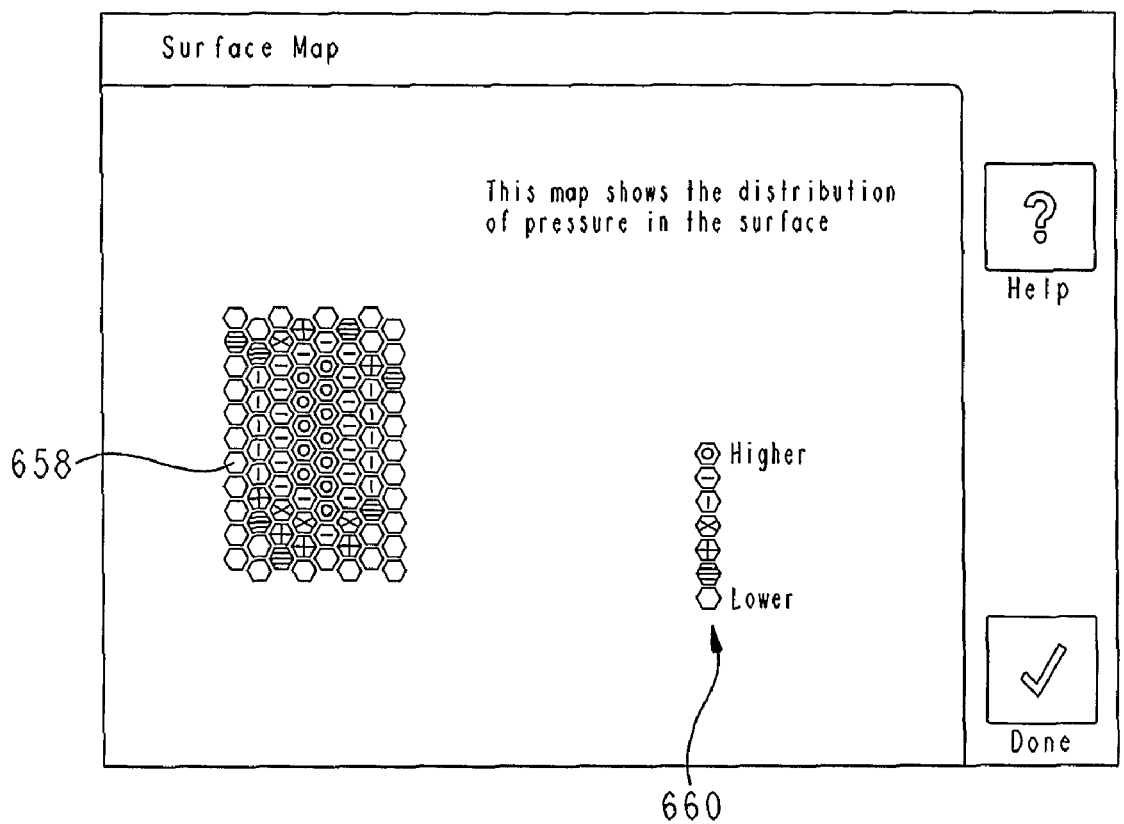
FIG. 27 is an exemplary user interface for a surface pressure map.

FIG. 27 shows a user interface display 640 for a surface map 658. The surface map 658 is a real-time or snapshot graphical depiction of the distribution of pressure applied to the surface 10. The legend 660 shows that darker colors are indicative of higher pressure while lower pressures are indicated by lighter colors in the illustrated embodiment. The example surface map 658 shown in FIG. 27 shows that pressure appears to be concentrated in the center of the mattress 10. The surface map 658 is updated in real time. For example, if a patient moves from a lying down position to a sitting position, the surface map will change to show a greater distribution of pressure in the seat section of the mattress. The surface map 658 may be used for clinical purposes, such as to allow an enduser to quickly assess a patient's risk of developing pressure ulcers, by showing graphically the areas of higher pressure. The surface map 658 may also be used by service technicians, for example, to configure or troubleshoot the mattress. Access to the surface map 658 may be restricted, for example, by requirement of a password.

In the illustrated embodiment, a firmness override or comfort adjust feature 642 is also provided. The firmness override feature allows a caregiver to adjust the internal bladder pressure of one or more air bladders in the mattress 10 for patient comfort. For example, if a particular patient prefers a firmer mattress, the internal bladder pressure may be increased. In the illustrated embodiment, the firmness override feature is provided in addition to the automatic pressure relief feature, but this may not always be the case. The firmness override feature is described in more detail in U.S. Provisional Patent Application Ser. No. 60/697,748, filed Jul. 8, 2005, and corresponding PCT Patent Application (Attorney Docket No. 8266-1561) filed on the same date herewith, assigned to the assignee of the present invention, and incorporated herein by reference.

The language menu item 644 enables the end user to configure the control unit user interface for a particular language, such as English, Spanish, or French.

The in service menu item 646 allows the end user to obtain information related to servicing of the mattress 10.

Figure 28B:
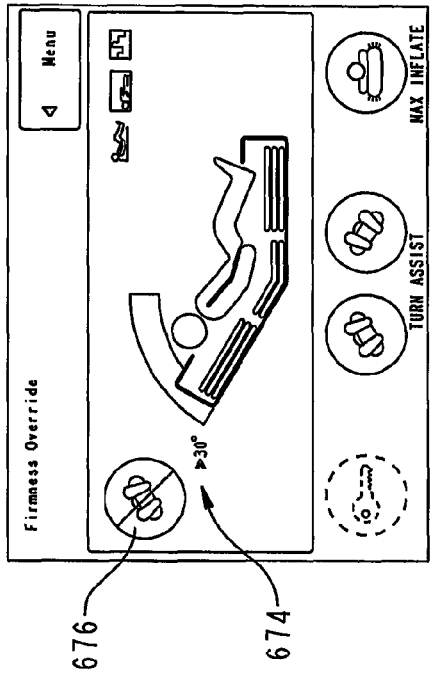
FIGS. 28 A-D are exemplary user interfaces for configuring a firmness override feature.
Figure 28D:
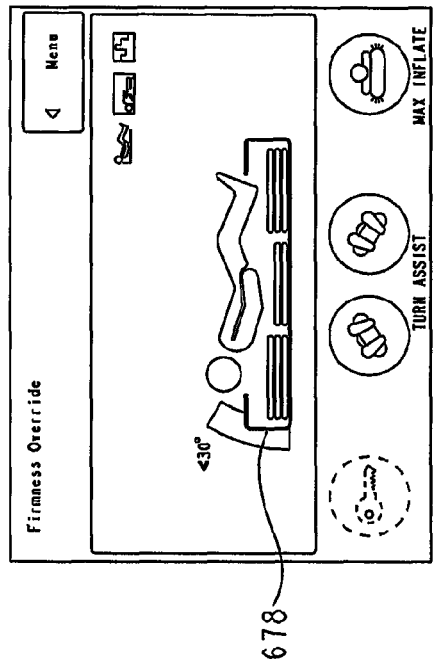
Figure 28A:
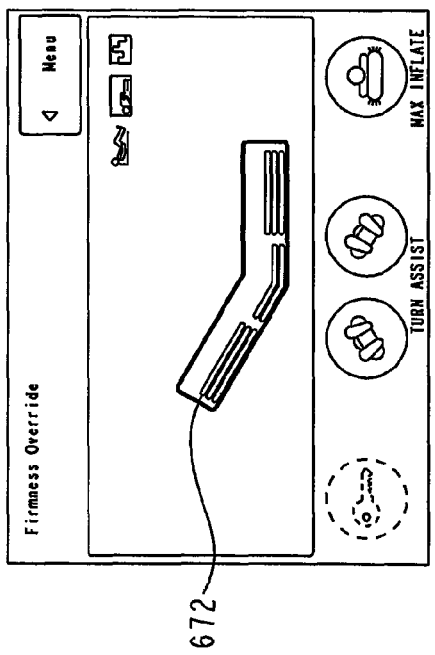
Figure 28C:
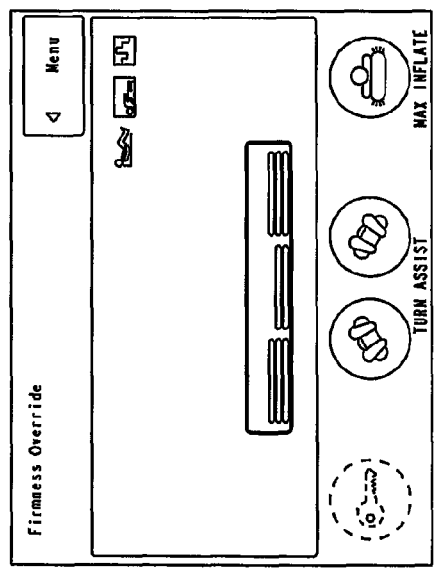

FIGS. 28A-D show example user interface display screens relating to the firmness override or comfort adjust feature 642. A graphical depiction of the mattress is provided, wherein one or more bars 672 are displayed within each portion of the mattress. The number wherein one or more bars 672 are displayed within each portion of the mattress. The number of bars corresponds to the relative internal pressure of the bladders in that particular section of the mattress. For example, in FIG. 28A, the bladder pressure is greater in the head section of the mattress and the foot section of the mattress and the pressure is lower in the seat section of the mattress. FIGS. 28B and 28D illustrate that if a patient is positioned on the mattress 10, the graphical depiction of the bed changes to include a patient. Also, if the head section of the mattress is elevated to an angle greater than thirty degrees, and a patient is present on the mattress 10, the graphical depiction changes again to indicate a no turn assist icon 676 and an angle indicator 674. The no turn assist icon 676 graphically indicates that the turn assist bladders may not be inflated while the mattress head angle is greater than thirty degrees. The angle indicator 674 graphically indicates whether the head angle is less than or greater than thirty degrees as shown in FIGS. 28B and 28D. These graphical depictions allow a caregiver or other end user to quickly assess the situation of a patient using the mattress 10. Also, these graphical indications provide a simplified way to communicate information to caregivers and end users who may speak different languages.

The in service menu item 646 also provides an online tutorial feature for caregivers, service technicians, and other end users. FIGS. 29A and 29B show examples of the online tutorial feature. In FIG. 29A, still graphics are provided to illustrate the use of the turn assist feature, for example. The graphics 662 are supplemented with text which provides an additional explanation. The end user can activate the show me button 664 to view an online video demonstration of a selected bed feature. When the show me button 664 is activated, a video 666 relating to the selected feature (i.e., turn assist), is played. A pause button 670 and a replay button 668 are provided to allow the end user to pause the playing of the video at any point or to replay the video.

FIGS. 30A-30F illustrate a sequence of example user interface displays that may be provided to communicate the status of an automatic pressure relief feature of the mattress 10 to an end user. An example automatic pressure relief feature is described in greater detail in U.S. patent application Ser. No. 11/119,991, filed May 2, 2004, assigned to the assignee of the present invention, and incorporated herein by reference. The graphical nature of the display shown in FIGS. 30A-30F enables the caregiver or other end user to quickly assess the status of the mattress 10 and the patient positioned thereon, as noted above. In the illustrated embodiment, when a new patient is first placed upon the mattress 10, the automatic pressure relief feature begins optimizing the pressure relief of the mattress 10 automatically. In FIG. 30A, the bars 680 indicate which section or sections of the mattress 10 are being optimized. FIGS. 30B and 30C show an example user interface display when the patient's head angle is greater than thirty degrees from horizontal. FIGS. 30D-30F are similar graphical displays for a patient on a mattress that is in the horizontal (unarticulated) position.

FIGS. 31A-31D show example user interface displays relating to the turn assist feature of the mattress 10. If a caregiver elects to activate one of the turn assist buttons 628, 630, but the bed has side rails and the side rails are in the down position, a warning window 682 will appear prompting the caregiver to raise the side rails to their full position before the turn assist feature will begin operating. FIG. 31D illustrates a user interface display that is shown if the caregiver selects the left turn assist button 628. This display graphically depicts a patient 684 being rotated to the left. A similar graphical depiction is provided in FIG. 31C for activation of the right turn assist feature 630. If the caregiver attempts to activate the turn assist feature 628, 630, but the head of the mattress 10 is elevated above an angle of thirty degrees from horizontal, then a pop up window such as shown in FIG. 31D is displayed. This display 686 includes an indication that the head angle of the mattress must be lowered below thirty degrees in order for the turn assist feature to be utilized. If the turn assist feature is already running when the head angle increases above thirty degrees, then the turn assist feature stops running. If the head section of the mattress is at an angle of less than thirty degrees from the horizontal position then no pop up window is displayed and the turn assist feature can continue.

Figure 32A:
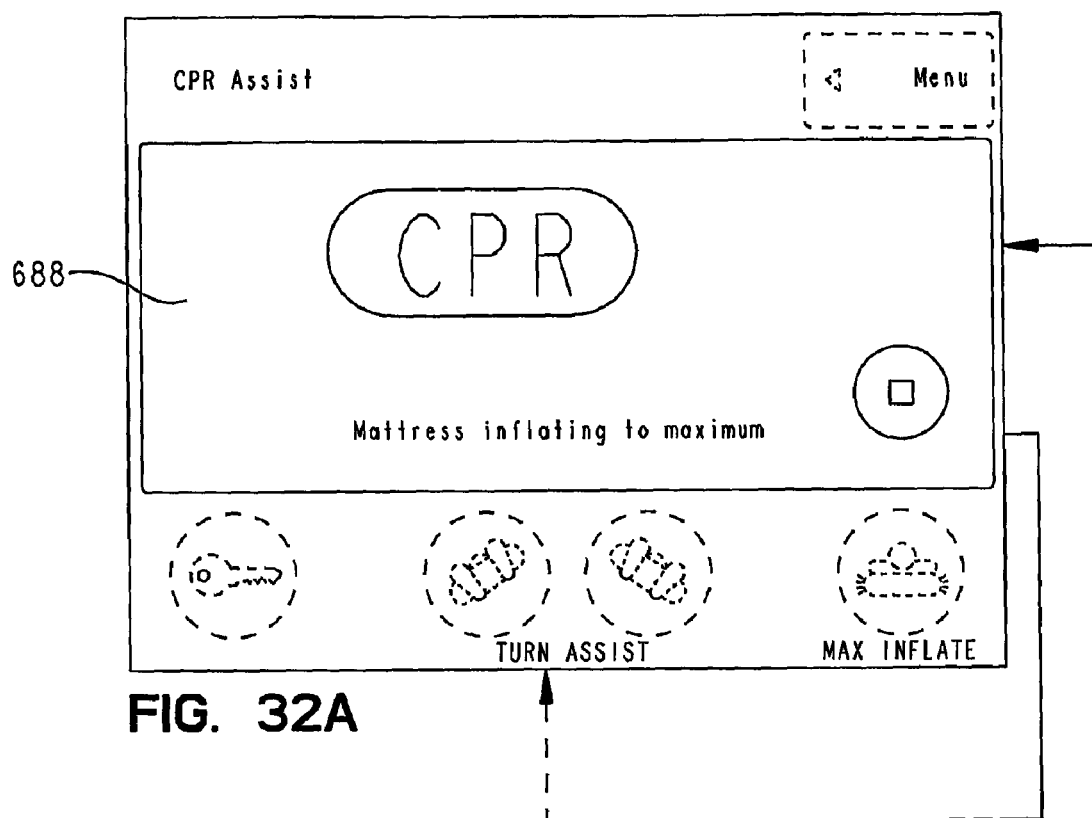
FIGS. 32 A-B are exemplary user interfaces for monitoring a CPR feature.
Figure 32B:
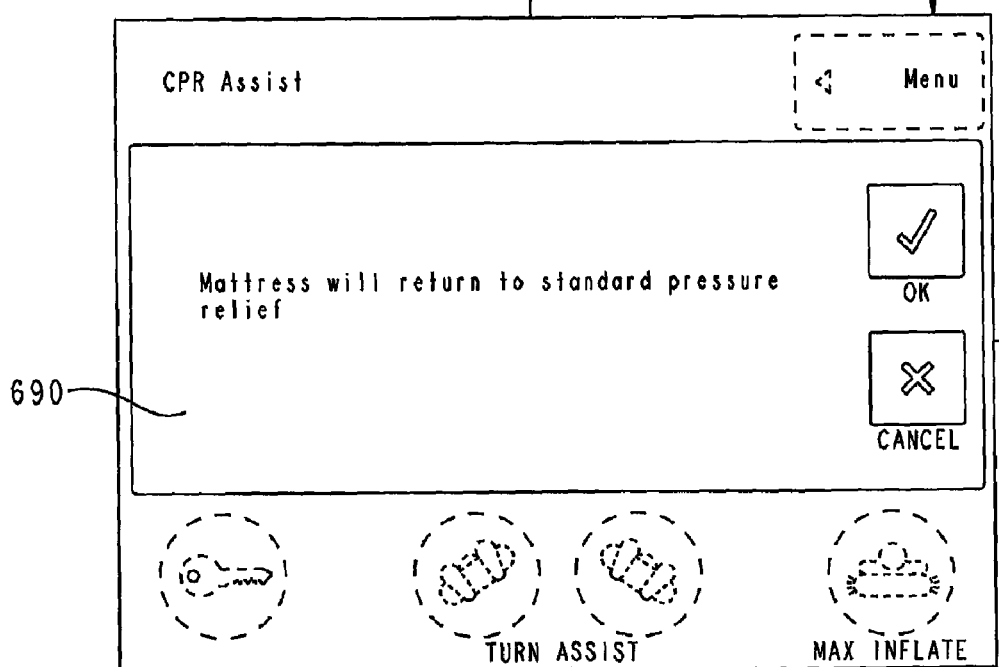

FIGS. 32A and 32B illustrate example graphical displays that would be presented to an end user on the display portion 24 if the CPR button 30 is activated or the maxinflate button 632 is activated. A message 688 is provided to indicate to the caregiver that the CPR or max inflate feature is in progress as shown in FIG. 32A. Once the CPR feature is completed, or after a period of time of no interaction, a second message 690 is displayed indicating that the mattress will now return to its standard pressure relief mode.

Figure 33:
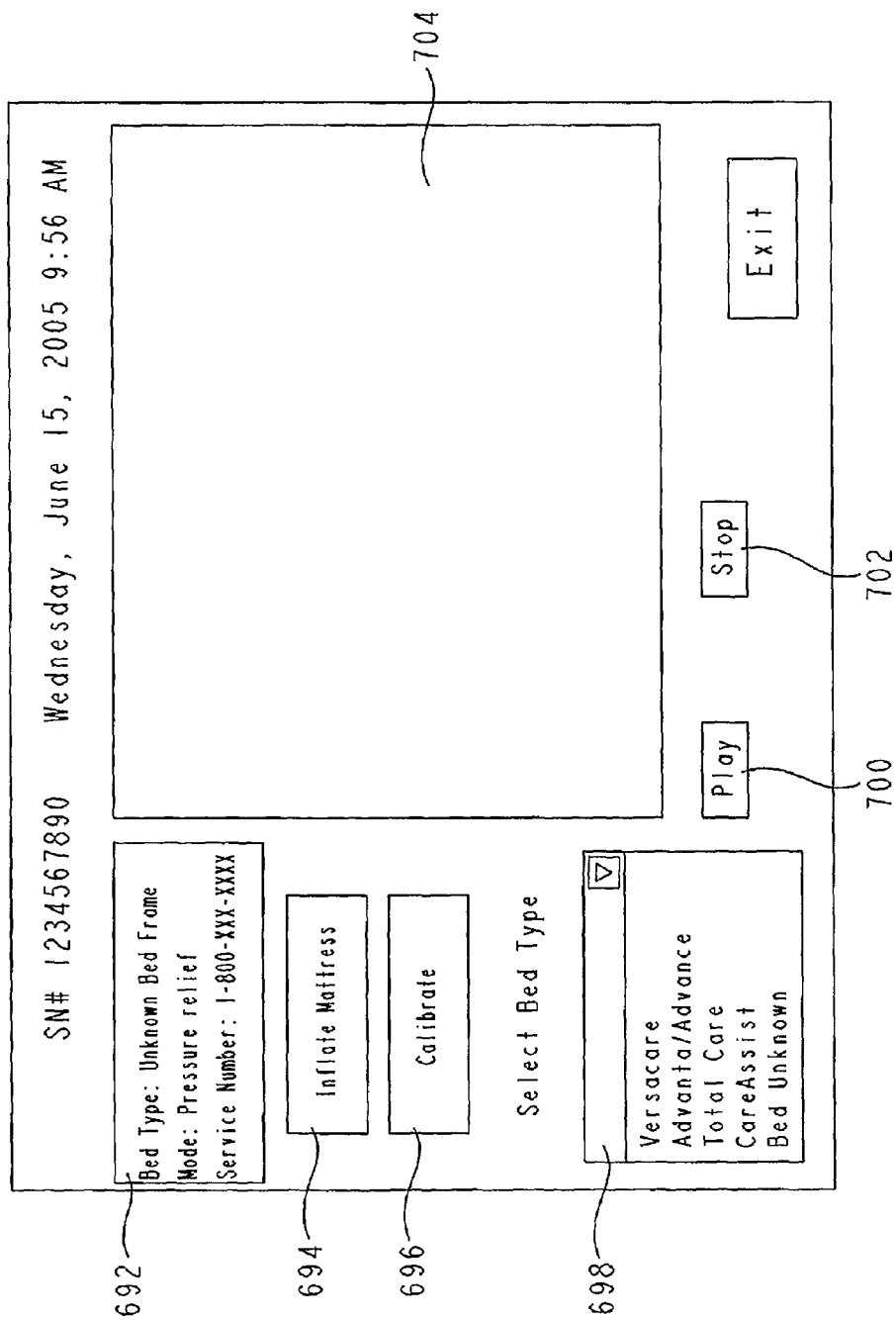
FIG. 33 is an exemplary user interface for initial mattress setup.

FIG. 33 is an example of a user interface for initially configuring the mattress 10, i.e., during installation. Such configuration is typically done by an authorized service technician. This screen and others may be password-protected or have access thereto otherwise restricted to authorized personnel.

General site-specific information is displayed in window 692, such as the type of bed frame on which the mattress 10 is being used, the service number to call for questions or problems, and the default operating mode for the mattress. In the illustrated embodiment, the default operating mode is the automatic pressure relief mode described above and also in U.S. patent application Ser. No. 11/119,991 incorporated herein by reference. The automatic pressure relief mode may be disabled, so that the mattress always maintains a preset bladder pressure, based on the patient's weight, for example.

Figure 34:
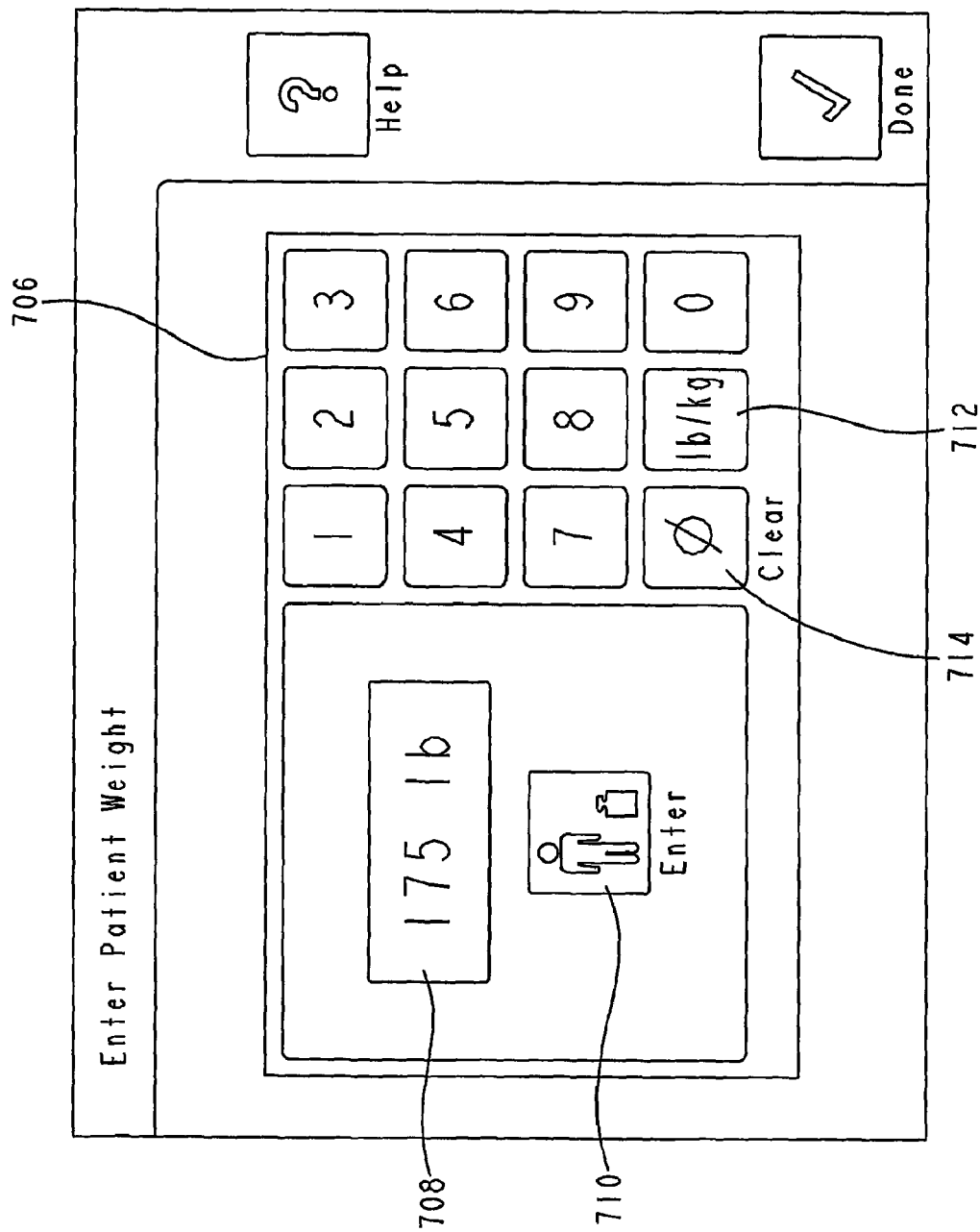
FIG. 34 is an exemplary user interface for entering patient weight.

FIG. 34 is an example of a user interface screen that may be displayed by control unit 42 for inputting a patient's weight. This screen may be password-protected or access otherwise restricted so that only authorized personnel can enter a patient weight. As shown, a numeric keypad 706 and digital display of the patient's weight 708 are provided. An "enter" key or similar mechanism 710 is provided such that activation thereof (i.e. by human touch) causes the entered weight value to be saved into the system. A "lb/kg" toggle button or similar mechanism 712 may be provided to enable entry of patient weight in either pounds or kilograms, or other suitable unit of measurement. A "clear" button 714 may be provided to enable the entered weight value to be modified or edited before it is finalized.

Menu 698 displays a list of bed frame choices from which to select the appropriate frame. Once the bed type is selected, the mattress may be inflated by activation of button 694, and one or more aspects of the pressure relief system (if applicable) may be calibrated by activation of button 696, in accordance with the selected bed type. Video display window 704 may display a video of a live demonstration to assist the end user in understanding how to perform mattress configuration, service, or other procedures. Play and stop buttons 700, 702 are provided to enable the end user to play or stop the video.

The present invention has been described with reference to certain exemplary embodiments, variations, and applications. However, the present invention is defined by the appended claims and therefore should not be limited by the described embodiments, variations, and applications.

The invention claimed is:

1. A control unit for a patient support, the control unit comprising:
    a housing adaptable to be removably coupled to a patient support, the housing defining an interior region including
    a controller,
    an air supply including a first portion operably coupled to the controller to provide high volume, low pressure air to a first interior portion of the patient support, and a second portion operably coupled to the controller to provide low volume, high pressure air to a second interior portion of the patient support,
    a user interface coupled to the housing, and
    a light bar coupled to the housing, the light bar being controllable by the controller to selectively illuminate in one of a plurality of modes,
    wherein each of the plurality of modes includes a color indicative of a different operating condition of the control unit.

2. The control unit of claim 1, wherein the first air supply portion includes a blower and the second air supply portion includes a compressor.

3. The control unit of claim 1, further comprising a hose connector coupled to the air supply.

4. The control unit of claim 3, wherein the hose connector includes a first connector portion coupled to the first air supply portion and a second connector portion coupled to the second air supply portion.

5. The control unit of claim 1, further comprising a display portion pivotably coupled to the housing.

6. The control unit of claim 1, further comprising a plurality of communication ports including a wireless connectivity port.

7. The control unit of claim 1, further comprising a memory port configured to receive a removable memory card.

8. The control unit of claim 1, further comprising an identification tag coupled to the housing.

9. The control unit of claim 1, further comprising a display portion pivotably coupled to the housing, the display portion being movable with respect to the housing between a raised position and a lowered position, the display portion including a video display and a touchscreen user interface.

10. The control unit of claim 9, wherein the display portion includes a wireless access port.

11. The control unit of claim 9, wherein the display portion includes a memory port configured to receive removable memory.

12. The control unit of claim 9, further comprising a friction hinge coupled between the display portion and the housing.

13. The control unit of claim 9, wherein the angle of the display portion with respect to the housing when the display portion is in the raised position is at least 180 degrees.

14. The control unit of claim 9, further comprising a detent configured to hold the display portion in the lowered position.

15. The control unit of claim 9, wherein the user interface includes a graphical depiction of a patient support which varies based on the presence or absence of a patient on the patient support.

16. The control unit of claim 1, further comprising a display portion configured to display a graphical user interface including at least one graphical depiction that automatically changes in response to a change in an operating condition of the patient support.

17. The control unit of claim 16, wherein the graphical depiction is of a patient support and the graphical depiction changes automatically in response to a person being positioned on the patient support.

18. The control unit of claim 16, wherein the graphical depiction is of a patient support and the graphical depiction changes automatically in response to articulation of a portion of the patient support.

19. The control unit of claim 16, wherein the graphical depiction is of a patient support and the graphical depiction changes automatically in response to a change in inflation of the patient support.

20. The control unit of claim 16, wherein the graphical depiction is of a pressure map for a patient support and the pressure map changes automatically in response to patient movement.

21. A control unit for a patient support, the control unit comprising:
- a housing adaptable to be removably coupled to a patient support, the housing defining an interior region including
- a controller,
- an air supply including a first portion operably coupled to the controller to provide high volume low pressure air to a first interior portion of the patient support and a second portion operably coupled to the controller to provide low volume, high pressure air to a second interior portion of the patient support,
- a user interface coupled to the housing, and
- a light bar coupled to the housing, the light bar being controllable by the controller to selectively illuminate in one of a plurality of modes,
- wherein the light bar illuminates in a first mode if the patient support is in CPR position.

22. The control unit of claim 21, wherein the light bar illuminates in a second mode if the control unit is in need of service.

23. The control unit of claim 22, wherein the light bar illuminates in a third mode if the control unit is powered on and operating normally.

24. The control unit of claim 23, wherein the light bar illuminates in a fourth mode if an alarm is activated.

* * * * *